US012679877B2

(12) United States Patent
Castillo et al.

(10) Patent No.: US 12,679,877 B2
(45) Date of Patent: Jul. 14, 2026

(54) NPRA AGONISTS, COMPOSITIONS, AND USES THEREOF

(71) Applicant: PharmaIn Corporation, Bothell, WA (US)

(72) Inventors: Gerardo M. Castillo, Bothell, WA (US); Akiko Nishimoto-Ashfield, Bothell, WA (US); Elijah M. Bolotin, Bothell, WA (US)

(73) Assignee: PharmaIN Corporation, Bothell, WA (US)

( * ) Notice: Subject to any disclaimer, the term of this patent is extended or adjusted under 35 U.S.C. 154(b) by 1057 days.

(21) Appl. No.: 16/577,947

(22) Filed: Sep. 20, 2019

(65) Prior Publication Data

US 2020/0017567 A1     Jan. 16, 2020

Related U.S. Application Data

(63) Continuation-in-part of application No. PCT/US2018/023491, filed on Mar. 21, 2018.

(60) Provisional application No. 62/475,147, filed on Mar. 22, 2017.

(51) Int. Cl.
| | |
|---|---|
| *C07K 14/575* | (2006.01) |
| *A61K 38/00* | (2006.01) |
| *A61K 47/54* | (2017.01) |
| *A61P 9/00* | (2006.01) |

(52) U.S. Cl.
CPC .......... *C07K 14/575* (2013.01); *A61K 47/542* (2017.08); *A61P 9/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 3,985,722 A | 10/1976 | Yoshida et al. | |
| 5,439,887 A | 8/1995 | Hamon et al. | |
| 6,660,271 B2 | 12/2003 | Kenten et al. | |
| 7,846,900 B2 | 12/2010 | Vesely | |
| 8,008,449 B2 | 8/2011 | Korman et al. | |
| 8,198,242 B2 * | 6/2012 | Wendt ..................... | A61P 9/12 514/21.3 |
| 8,217,149 B2 | 7/2012 | Irving et al. | |
| 8,551,937 B2 * | 10/2013 | Wakabayashi ......... | C07K 16/26 530/300 |
| 9,745,344 B2 | 8/2017 | Osterkamp et al. | |
| 9,759,725 B2 | 9/2017 | Nelson et al. | |
| 10,010,613 B2 | 7/2018 | Castillo et al. | |
| 10,035,885 B2 | 7/2018 | Jones et al. | |
| 10,507,248 B2 | 12/2019 | Castillo et al. | |
| 2001/0027181 A1 | 10/2001 | Kitakaze | |
| 2004/0138134 A1 | 7/2004 | Golembo et al. | |

| | | | |
|---|---|---|---|
| 2009/0092582 A1 * | 4/2009 | Bogin ..................... | A61P 17/06 435/69.51 |
| 2009/0170196 A1 | 7/2009 | Vesely | |
| 2010/0254943 A1 | 10/2010 | Grabstein et al. | |
| 2010/0297021 A1 | 11/2010 | Wendt et al. | |
| 2010/0310561 A1 | 12/2010 | Canada et al. | |
| 2010/0331256 A1 | 12/2010 | Wendt et al. | |
| 2012/0164142 A1 | 6/2012 | Crine et al. | |
| 2012/0220528 A1 | 8/2012 | Van Antwerp et al. | |
| 2014/0072557 A1 | 3/2014 | Kangawa et al. | |
| 2014/0248269 A1 | 9/2014 | Kangawa et al. | |
| 2015/0125457 A1 | 5/2015 | Wakabayashi et al. | |
| 2015/0174201 A1 | 6/2015 | Geimer | |
| 2015/0307578 A1 | 10/2015 | Castillo et al. | |
| 2016/0122386 A1 | 5/2016 | Wisniewski et al. | |
| 2017/0196931 A1 | 7/2017 | Chawla | |

(Continued)

FOREIGN PATENT DOCUMENTS

| | | |
|---|---|---|
| CN | 1199097 A | 11/1998 |
| EP | 0037516 B1 | 9/1984 |

(Continued)

OTHER PUBLICATIONS

Ostergaard et al. Scientific Reports, 2021, 11:21179.*
Office Action mailed Apr. 28. 2022 issued in counterpart Vietnamese Application No., 1-2019-05781 filed Mar. 21, 2018 (3 pages).
European Supplementary Search Report mailed Dec. 16, 2020, issued in corresponding European Application No. 18771099.1, filed Mar. 21, 2018, 7 pages.
International Search Report and Written Opinion mailed May 17, 2018, issued in corresponding International Application No. PCT/US2018/23491, filed Mar. 21, 2018, 9 pages.
International Preliminary Report on Patentability mailed Oct. 3, 2019, issued in corresponding European Application No. PCT/US2018/023491, filed Mar. 21, 2018, 7 pages.

(Continued)

*Primary Examiner* — Tara L Martinez

(74) *Attorney, Agent, or Firm* — Hamilton, Brook, Smith & Reynolds, P.C.

(57) ABSTRACT

This disclosure provides a natriuretic peptide derivative of Formula (I), and to compositions including a natriuretic peptide derivative of Formula (I), $$\text{(fatty acyl)}_z\text{-(B)}_x\text{-(G)}_y\text{-NP} \qquad \text{(I),}$$

wherein: z is 1, x is an integer from 2 to 4 and y is 3; or z is 0, x is an integer from 0 to 4 and y is an integer from 1 to 3; fatty acyl comprises from 12 to 24 (e.g., 12 to 18) carbons atoms; B is lysine or arginine; G is glycine; NP is a natriuretic peptide; if present, (fatty acyl)$_z$- is covalently linked to the N-terminus of (B)$_x$; (fatty acyl)$_z$-(B)$_x$— is covalently linked to the N-terminus of (G)$_y$; and (fatty acyl)$_z$-(B)$_x$-(G)$_y$- is covalently linked to the N-terminus of NP. The natriuretic peptide derivative according to the disclosure, and compositions thereof, are useful in the treatment of diseases such as hypertension, vascular congestion, and heart disease.

7 Claims, No Drawings

Specification includes a Sequence Listing.

(56) References Cited

U.S. PATENT DOCUMENTS

| | | | |
|---|---|---|---|
| 2017/0368190 A1 | 12/2017 | Castillo et al. | |
| 2019/0015481 A1 | 1/2019 | Rau et al. | |
| 2019/0255183 A1 | 8/2019 | Sprogøe et al. | |
| 2019/0328840 A1 | 10/2019 | Sprogøe et al. | |
| 2020/0246434 A1 | 8/2020 | Bullens et al. | |
| 2021/0079056 A1 | 3/2021 | Brockschnieder et al. | |
| 2023/0241164 A1 | 8/2023 | Tachibana et al. | |
| 2023/0416328 A1 | 12/2023 | Tachibana et al. | |

FOREIGN PATENT DOCUMENTS

| | | | |
|---|---|---|---|
| EP | 2682128 A1 | 1/2014 | |
| EP | 2745846 A1 | 6/2014 | |
| EP | 3189835 B1 | 7/2018 | |
| EP | 3553079 A1 | 10/2019 | |
| JP | 2018-522022 A | 8/2018 | |
| JP | 2020-511494 A | 4/2020 | |
| WO | 99/42472 A1 | 8/1999 | |
| WO | 02/74234 A2 | 9/2002 | |
| WO | WO2004-047871 | * | 7/2004 |
| WO | 2008/154226 A1 | 12/2008 | |
| WO | 2008/156712 A1 | 12/2008 | |
| WO | 2009067639 A2 | 5/2009 | |
| WO | 2010/129655 A2 | 11/2010 | |
| WO | 2011/066389 A1 | 6/2011 | |
| WO | 2011/075471 A2 | 6/2011 | |
| WO | 2012/088608 A1 | 7/2012 | |
| WO | 2012/118042 A1 | 9/2012 | |
| WO | 2013/027680 A1 | 2/2013 | |
| WO | 2013/151767 A1 | 10/2013 | |
| WO | 2016/077143 A1 | 5/2016 | |
| WO | 2017/082186 A1 | 5/2017 | |
| WO | 2018/175534 A1 | 9/2018 | |

OTHER PUBLICATIONS

Gupta, D., et al., "Natriuretic Peptides and Cardiometabolic Health", Circulation Journal, vol. 79, No. 8, 2015, pp. 1647-1655.

Abraham et al., Neutrophils as early immunologic effectors in hemorrhage- or endotoxemia-induced acute lung injury, Am. J. Physiol. Lung Cell. Mol. Physiol. 279: 1137-1145, 2000.

Apodaca, M.C. et al., "Characterization of a whole blood assay for quantifying myeloid-derived suppressor cells," Journal of Immunotherapy of Cancer, vol. 7; 230; 11 Pages (2019).

Biernacka, A. et al., "TGF-β signaling in fibrosis," Growth Factors, vol. 29; No. 5; 196-202 (2011).

Black et al., Renal Inflammation and Fibrosis: A Double-edged Sword, Journal of Histochemistry & Cytochemistry 2019, vol. 67(9) 663-681.

Brooks et al., Regulation of mitochondrial dynamics in acute kidney injury in cell culture and rodent models. J Clin Invest 2009; 119: 1275-85.

Bruno, T.C. et al., "Antigen-presenting intratumoral B cells affect CD4+ TIL phenotypes in non-small cell lung cancer patients," Cancer Immunol. Res., vol. 5; No. 10; 898-907 (2017).

Castillo et al., Extending residence time and stability of peptides by Protected Graft Copolymer (PGC) excipient: GLP-1 example, Pharm. Res., (2012) 29(1); p. 306-18.

Castillo et al., Protected graft copolymer-formulated fibroblast growth factors mitigate the lethality of partial body irradiation injury, PLoS One, (2017) 12(2); e0171703.

Castillo, G. et al., "Extending residence time and stability of peptides by Protected Graft Copolymer (PGC) excipient: GLP-1 example," Pharm Res., vol. 29; No. 1; 306-318 (2012).

Castillo, G.M. et al., "Protected graft copolymer-formulated fibroblast growth factors mitigate the lethality of partial body irradiation injury," PLoS ONE, vol. 12; No. 2; e0171703; 25 pages (2017).

Chopra, S. et al., "Physiology and clinical significance of natriuretic hormones," Indian Journal of Endocrinology and Metabolism, vol. 17; Issue 1; 83-90 (2013).

Chrisman et al., Seminal Plasma Factors That Cause Large Elevations in Cellular Cyclic GMP Are C-type Natriuretic Peptides, J. Biol. Chem. 1993; 268:3698-3703.

Chrisman, T.D. et al., "Seminal Plasma Factors That Cause Large Elevations in Cellular Cyclic GMP Are C-type Natriuretic Peptides," Journal of Biological Chemistry, vol. 268; No. 5; 3698-3703 (1993).

Clayton, K.L. et al., "T-cell immunoglobulin and mucin domain-containing protein 3 (Tim-3) is recruited to the immune synapse, disrupts stable synapse formation and associates with receptor phosphatases," J Immunol., vol. 192; No. 2; 782-791 (2014).

Collard, H.R., et al., Plasma biomarker profiles in acute exacerbation of idiopathic pulmony fibrosis, American Journal of Physiology; Lung Cellular and Molecular Physiology, 2010 299: L3-L7.

Das, B.B. and Solinger, R., "Role of Natriuretic Peptide Family in Cardiovascular Medicine," Cardiovascular & Hematological Agents in Medicinal Chemistry, vol. 7; 29-42 (2009).

Flick et al., Leukocytes Are Required for Increased Lung Microvascular Permeability after Microembolization in Sheep, Circ. Res. 48:344-351, 1981.

Gao, G.F. and Jakobsen, B.K., "Molecular interactions of coreceptor CD8 and MHC class I: the molecular basis for functional coordination with the T-cell receptor," Immunology Today, vol. 21; No. 12; 630-636 (2000).

Goaddard, J.C et al., "A computer image analysis system for microvessel density measurement in solid tumours," Angiogenesis, vol. 5; 15-20 (2002).

Gul et al., Changing Definitions of Sepsis, Turk J Anaesthesiol Reanim. Jun. 2017; 45(3): 129-138.

Hamid, O. et al., "Safety and Tumor Responses with Lambrolizumab (Anti-PD-1) in Melanoma," N Eng J Med., vol. 369; No. 2; 134-144 (2013).

Han, H., et al., Thymic Stromal Lymphopoietin Amplifies the Differentiation of Alternatively Activated Macrophages, Journal of Immunology, 2013, 190:904-912.

Harbeck RJ, Immunophenotyping of Bronchoalveolar Lavage Lymphocytes, Clin Diagn Lab Immunol. 1998, 5(3):271-7.

Hasnis, E. et al., "Anti-Bv8 Antibody and Metronomic Gemcitabine Improve Pancreatic Adenocarcinoma Treatment Outcome Following Weekly Gemcitabine Therapy," Neoplasia, vol. 16; 501-510 (2014).

Heflin A C Jr and Brigham K L., Prevention by granulocyte depletion of increased vascular permeability of sheep lung following endotoxemia, J. Clin. Invest. 68:1253-1260, 1981.

Hendrickson, C.M. and Matthay, M.A., Viral Pathogens and Acute Lung Injury: Investigation Inspired by the SARS Epidemic and the 2009 H1N1 Influenza Pandemic, Semin Respir Grit Care Med, vol. 34; 475-486 (2013).

Hunt, P.J. et al., "Bioactivity and Metabolism of C-Type Natriuretic Peptide in Normal Man," Journal of Clinical Endocrinology and Metabolism, vol. 78; No. 6; 1428-1435 (1994).

Igaki et al., Effects of Intravenously Administered C-type Natriuretic Peptide in Humans: Comparison with Atrial Natriuretic Peptide, Hypertens Res 1998; 21: 7-13.

Imura, H. et al., "The Natriuretic Peptide System in the Brain: Implication in the Central Control of Cardiovascular and Neuroendocrine Functions," Frontiers in Neuroendocrinology, vol. 13; No. 3; 217-249 (1992).

International Search Report and Written Opinion received for PCT Patent Application No. PCT/US2021/037031, mailed on Jan. 31, 2022, 19 pages.

International Search Report and Written Opinion received for PCT Patent Application No. PCT/US2021/037061, mailed on Dec. 8, 2021, 17 pages.

Ise, W. et al., "T Follicular Helper Cell-Germinal Center B Cell Interaction Strength Regulates Entry into Plasma Cell or Recycling Germinal Center Cell Fate," Immunity, vol. 48; 702-715 (2018).

Itoh, H. and Nakao, K., "Natriuretic peptide system," Nihon Rinsho., vol. 55; 1923-1936 (1997). (English Abstract Attached).

Kimura, T. et al., "C-type natriuretic peptide ameliorates pulmonary fibrosis by acting on lung fibroblasts in mice," Respiratory Research, vol. 17; No. 19; 17 pages (2016).

Kimura, T. et al., "C-type natriuretic peptide attenuates lipopolysaccharide-induced acute lung injury in mice," Journal of Surgical Research, vol. 194; 631-637 (2015).

(56)         References Cited

OTHER PUBLICATIONS

Koller, K.J. et al., "Selective Activation of the B Natriuretic Peptide Receptor by C-Type Natriuretic Peptide," Science, vol. 252; 120-123 (1991).

Li, W. et al., "Monitoring of tumor vascular normalization: the key points from basic research to clinical application," Cancer Management and Research, vol. 10; 4163-4172 (2018).

Li, Y-T., et al., Monocyte Chemoattractant Protein-1, a Possible Biomarker of Multiorgan Failure and Mortality in Ventilator-Associated Pneumonia, International Journal of Molecular Sciences, 2019:20 (9): 2218.

Lumsden, N.G. et al., "C-Type Natriuretic Peptide (CNP): Cardiovascular Roles and Potential as a Therapeutic Target," Curr Pharm Des., vol. 16; No. 37; 4080-4088 (2010).

Malyszko et al., Kozlowska K, Kozlowski L, Malyszko J. Nephrotoxicity of anticancer treatment. Nephrol Dial Transplant 2017; 32: 924-36.

Matsumoto et.al., An improved mouse model that rapidly develops fibrosis in non-alcoholic steatohepatitis, Int J Exp Pathol. Apr. 2013; 94(2):93-103.

Mellman, I. et al., "Cancer immunotherapy comes of age," Nature, vol. 480; No. 7378; 480-489 (2011).

Miller et al., Mechanisms of cisplatin nephrotoxicity. Toxins (Basel) 2010; 2: 2490-518.

Mkrtichyan, M. et al., "B7-DC-Ig Enhances Vaccine Effect by a Novel Mechanism Dependent on PD-1 Expression Level on T Cell Subsets," Journal of Immunol., vol. 189; No. 5; 2338-2347 (2012).

Nagase, M. et al., "Tissue distribution and localization of natriuretic peptide receptor subtypes in stroke-prone spontaneously hypertensive rats," Journal of Hypertension, vol. 15; 1235-1243 (1997).

Notification Concerning Transmittal of International Preliminary Report on Patentability for International Application No. PCT/US2021/037061; mailed Dec. 22, 2022.

Nuglozeh, E. and Kozak, L.P., "Genetic mapping of the C-type natriuretic peptide receptor (Npr2) gene to mouse Chromosome 4," Mammalian Genome, vol. 8; 624-625 (1997).

O hAinmhire, E. and Humphreys, B.D., "Fibrotic Changes Mediating Acute Kidney Injury to Chronic Kidney Disease Transition," Nephron, vol. 137; 264-267 (2017).

Ogawa, Y. et al., "Molecular Cloning and Chromosomal Assignment of the Mouse C-Type Natriuretic Peptide (CNP) Gene (Nppc): Comparison with the Human CNP Gene (NPPC)," Genomics, vol. 24; 383-387 (1994).

Ogawa, Y. et al., "Molecular Cloning of the Complementary DNA and Gene That Encode Mouse Brain Natriuretic Peptide and Generation of Transgenic Mice That Overexpress the Brain Natriuretic Peptide Gene," J Clin. Invest., vol. 93; 1911-1921 (1994).

Pardoll, D.M., "The blockade of immune checkpoints in cancer immunotherapy," Nat Rev Cancer, vol. 12; No. 4; 252-264 (2012).

Park, J. et al., "Normalization of Tumor Vessels by Tie2 Activation and Ang2 Inhibition Enhances Drug Delivery and Produces a Favorable Tumor Microenvironment," Cancerl Cell, vol. 30; 953-967 (2016).

Peng, Y. et al., "Critical roles of miRNA-mediated regulation of TGFb signalling during mouse cardiogenesis," Cardiovascular Research, vol. 103; No. 2; 258-267 (2014).

Perazella M.A., Onco-nephrology: renal toxicities of chemotherapeutic agents. Clin J Am Soc Nephrol 2012; 7: 1713-21.

Potter, L.R. and Hunter, T., "Guanylyl Cyclase-linked Natriuretic Peptide Receptors: Structure and Regulation," The Journal of Biological Chemistry, vol. 276; No. 9; 6057-6060 (2001).

Potter, L.R., "Natriuretic Peptide Metabolism, Clearance and Degradation," FEBS J., vol. 278; No. 11; 1808-1817 (2011).

Ribas, A. et al., "Phase III Randomized Clinical Trial Comparing Tremelimumab With Standard-of-Care Chemotherapy in Patients With Advanced Melanoma," Journal of Clinical Oncology, vol. 31; No. 5; 7 Pages (2013).

Rosenblatt, J. et al., "PD-1 blockade by CT-011, anti PD-1 antibody, enhances ex-vivo T cell responses to autologous dendritic/myeloma fusion vaccine," J Immunother., vol. 34; No. 5; 409-418 (2011).

Schulz, S. et al., "The Primary Structure of a Plasma Membrane Guanylate Cyclase Demonstrates Diversity within This New Receptor Family," Cell, vol. 58; 1155-1162 (1989).

Schupp, J.C., et al., Macrophage Activation in Acute Exacerbation of Idiopathic Pulmonary Fibrosis, PLoS One, 2015 10(1): e0116775.

Sheth et al., Mechanisms of Cisplatin-Induced Ototoxicity and Otoprotection, Frontiers in Cellular Neuroscience, Oct. 27, vol. 11, 2017.

Singer et al., The Third International Consensus Definitions for Sepsis and Septic Shock (Sepsis-3), JAMA 2016; 315(8): 801-810.

Sudoh, T. et al., "Cloning nd Sequence Analysis of cDNA Encoding a Precursor for Human Brain Natriuretic Peptide," Biochemical and Biophysical Research Communications, vol. 159; No. 3; 1427-1434 (1989).

Suga, S. et al., "Receptor Selectivity of Natriuretic Peptide Family, Atrial Natriuretic Peptide, Brain Natriuretic Peptide, and C-Type Natriuretic Peptide," Endocrinology, vol. 130; No. 1; 229-239 (1992).

Suga, S. et al., "Regulation of Endothelial Production of C-Type Natriuretic Peptide by Interaction between Endothelial Cells and Macrophages," Endocrinology, vol. 139; No. 4; 1920-1926 (1998).

Tang, M., et al., TNF-a Mediated Increase of HIF-1a Inhibits VASP Expression, Which Reduces Alveolar-Capillary Barrier Function during Acute Lung Injury (ALI), PLoS One, Jul. 22, 2014;9(7):e102967.

Topalian, S.L. et al., "Safety, Activity, and Immune Correlates of Anti-PD-1 Antibody in Cancer," The New England Journal of Medicine, vol. 366; No. 26; 43-54 (2012).

Vesely, B.A. et al., "Five cardiac hormones decrease the number of human small-cell lung cancer cells," European Journal of Clinical Investigation, vol. 35; 388-398 (2005).

Vesely, B.A. et al., "Four peptide hormones decrease the number of human breast adenocarcinoma cells," European Journal of Clinical Investigation, vol. 35; 60-69 (2005).

Vesely, D.L., "Metabolic Targets of Cardiac Hormones' Therapeutic Anti-Cancer Effects," Current Pharmaceutical Design, vol. 16; 1159-1166 (2010).

Wendt, D.J. et al., "Neutral Endopeptidase-Resistant C-Type Natriuretic Peptide Variant Represents a New Therapeutic Approach for Treatment of Fibroblast Growth Factor Receptor 3-Related Dwarfism," The Journal of Pharmacology and Experimental Therapeutics, vol. 353; 132-149 (2015).

Wisniewski, K. et al., "New, Potent, Selective, and Short-Acting Peptidic V1a Receptor Agonists," Journal of Medicinal Chemistry, vol. 54; 4388-4398 (2011).

Wu, K. et al., "Structural Basis of a Flavivirus Recognized by Its Neutralizing Antibody," The Journal of Biological Chemistry, vol. 278; No. 46; 46007-46013 (2003).

Yu et al., Current Strategies to Combat Cisplatin-Induced Ototoxicity Front. Pharmacol., Jul. 3, 2020; 12 pages.

Zenitani, M. et al., "C-type natriuretic peptide in combination with sildenafil attenuates proliferation of rhabdomyosarcoma cells," Cancer Medicine, vol. 5; No. 5; 795-805 (2016).

Zhao, Y. et al., "Losartan treatment enhances chemotherapy efficacy and reduces ascites in ovarian cancer models by normalizing the tumor stroma," PNAS, vol. 116; No. 6; 2210-2219 (2019).

Bogdanov et al., "Protected Graft Copolymer (PGC) in Imaging and Therapy: A Platform for the Delivery of Covalently and Non-Covalently Bound Drugs", Theranostics, vol. 2, No. 6, Jun. 4, 2012, pp. 553-576.

Breinholt et al. TransCon CNP, a Sustained-Release C-Type Natriuretic Peptide Prodrug, a Potentially Safe and Efficacious New Therapeutic Modality for the Treatment of Comorbidities Associated with FGF Receptor 3-Related Skeletal Dysplasias, J Pharmacol. Exp. Ther., vol. 370, No. 3, Sep. 2019, pp. 459-471.

Forsberg et al. HER2 CAR-T Cells Eradicate Uveal Melanoma and T-cell Therapy-Resistant Human Melanoma in IL2 Transgenic NOD/SCID IL2 Receptor Knockout Mice. Cancer Res. Mar. 1, 2019; 79(5):899-904 (Year: 2019).

Khair et al. Combining Immune Checkpoint Inhibitors: Established and Emerging Targets and Strategies to Improve Outcomes in Melanoma. Front Immunol. Mar. 19, 2019; 10:453 (Year: 2019).

(56) References Cited

OTHER PUBLICATIONS

Kimura et al., "C-type natriuretic peptide ameliorates pulmonary fibrosis by acting on lung fibroblasts in mice", Respiratory Research, vol. 17, No. 19, 2016, 17 pages.
Murakami et al., "C-type natriuretic peptide attenuates bleomycin-induced pulmonary fibrosis in mice", American Journal of Physiology Lung Cellular and Molecular Physiology, vol. 287, No. 6, 2004, pp. L1172-L1177.
Non-Final Office Action received for U.S. Appl. No. 18/009,596, mailed on Nov. 21, 2025, 33 pages.

* cited by examiner

```
                            SEQUENCE LISTING

<160> NUMBER OF SEQ ID NOS: 159

<210> SEQ ID NO 1
<211> LENGTH: 28
<212> TYPE: PRT
<213> ORGANISM: Homo Sapiens

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 29
<212> TYPE: PRT
<213> ORGANISM: Homo Sapiens

<400> SEQUENCE: 2

Gly Ser Leu Arg Arg Ser Ser Cys Phe Gly Gly Arg Met Asp Arg Ile
1               5                   10                  15

Gly Ala Gln Ser Gly Leu Gly Cys Asn Ser Phe Arg Tyr
            20                  25

<210> SEQ ID NO 3
<211> LENGTH: 30
<212> TYPE: PRT
<213> ORGANISM: Homo Sapiens

<400> SEQUENCE: 3

Gly Gly Ser Leu Arg Arg Ser Ser Cys Phe Gly Gly Arg Met Asp Arg
1               5                   10                  15

Ile Gly Ala Gln Ser Gly Leu Gly Cys Asn Ser Phe Arg Tyr
            20                  25                  30

<210> SEQ ID NO 4
<211> LENGTH: 31
<212> TYPE: PRT
<213> ORGANISM: Homo Sapiens

<400> SEQUENCE: 4

Gly Gly Gly Ser Leu Arg Arg Ser Ser Cys Phe Gly Gly Arg Met Asp
1               5                   10                  15
```

-continued

```
Arg Ile Gly Ala Gln Ser Gly Leu Gly Cys Asn Ser Phe Arg Tyr
        20                  25                  30

<210> SEQ ID NO 5
<211> LENGTH: 32
<212> TYPE: PRT
<213> ORGANISM: Homo Sapiens

<400> SEQUENCE: 5

Lys Gly Gly Gly Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
        20                  25                  30

<210> SEQ ID NO 6
<211> LENGTH: 33
<212> TYPE: PRT
<213> ORGANISM: Homo Sapiens

<400> SEQUENCE: 6

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
        20                  25                  30

Tyr

<210> SEQ ID NO 7
<211> LENGTH: 34
<212> TYPE: PRT
<213> ORGANISM: Homo Sapiens

<400> SEQUENCE: 7

Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
        20                  25                  30

Arg Tyr

<210> SEQ ID NO 8
<211> LENGTH: 35
<212> TYPE: PRT
<213> ORGANISM: Homo Sapiens

<400> SEQUENCE: 8

Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
        20                  25                  30

Phe Arg Tyr
        35

<210> SEQ ID NO 9
<211> LENGTH: 33
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 9
```

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 10
<211> LENGTH: 33
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified byCH3(CH2)16CO

<400> SEQUENCE: 10

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 11
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 11

Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr

<210> SEQ ID NO 12
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 12

Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr

<210> SEQ ID NO 13
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 13

```
Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr
```

<210> SEQ ID NO 14
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 14

```
Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr
```

<210> SEQ ID NO 15
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 15

```
Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30

Phe Arg Tyr
        35
```

<210> SEQ ID NO 16
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 16

```
Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30

Phe Arg Tyr
        35
```

<210> SEQ ID NO 17
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)

<223> OTHER INFORMATION: Modified by CH3(CH2)14CO

<400> SEQUENCE: 17

Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30

Phe Arg Tyr
        35

<210> SEQ ID NO 18
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 18

Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30

Phe Arg Tyr
        35

<210> SEQ ID NO 19
<211> LENGTH: 28
<212> TYPE: PRT
<213> ORGANISM: Rattus norvegicus

<400> SEQUENCE: 19

Ser Leu Arg Arg Ser Ser Cys Phe Gly Gly Arg Ile Asp Arg Ile Gly
1               5                   10                  15

Ala Gln Ser Gly Leu Gly Cys Asn Ser Phe Arg Tyr
            20                  25

<210> SEQ ID NO 20
<211> LENGTH: 29
<212> TYPE: PRT
<213> ORGANISM: Rattus norvegicus

<400> SEQUENCE: 20

Gly Ser Leu Arg Arg Ser Ser Cys Phe Gly Gly Arg Ile Asp Arg Ile
1               5                   10                  15

Gly Ala Gln Ser Gly Leu Gly Cys Asn Ser Phe Arg Tyr
            20                  25

<210> SEQ ID NO 21
<211> LENGTH: 30
<212> TYPE: PRT
<213> ORGANISM: Rattus norvegicus

<400> SEQUENCE: 21

Gly Gly Ser Leu Arg Arg Ser Ser Cys Phe Gly Gly Arg Ile Asp Arg
1               5                   10                  15

Ile Gly Ala Gln Ser Gly Leu Gly Cys Asn Ser Phe Arg Tyr
            20                  25                  30

<210> SEQ ID NO 22
<211> LENGTH: 31

```
<212> TYPE: PRT
<213> ORGANISM: Rattus norvegicus

<400> SEQUENCE: 22

Gly Gly Gly Ser Leu Arg Arg Ser Ser Cys Phe Gly Gly Arg Ile Asp
1               5                   10                  15

Arg Ile Gly Ala Gln Ser Gly Leu Gly Cys Asn Ser Phe Arg Tyr
            20                  25                  30

<210> SEQ ID NO 23
<211> LENGTH: 32
<212> TYPE: PRT
<213> ORGANISM: Rattus norvegicus

<400> SEQUENCE: 23

Lys Gly Gly Gly Ser Leu Arg Arg Ser Ser Cys Phe Gly Gly Arg Ile
1               5                   10                  15

Asp Arg Ile Gly Ala Gln Ser Gly Leu Gly Cys Asn Ser Phe Arg Tyr
            20                  25                  30

<210> SEQ ID NO 24
<211> LENGTH: 33
<212> TYPE: PRT
<213> ORGANISM: Rattus norvegicus

<400> SEQUENCE: 24

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30

Tyr

<210> SEQ ID NO 25
<211> LENGTH: 34
<212> TYPE: PRT
<213> ORGANISM: Rattus norvegicus

<400> SEQUENCE: 25

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 26
<211> LENGTH: 35
<212> TYPE: PRT
<213> ORGANISM: Rattus norvegicus

<400> SEQUENCE: 26

Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35

<210> SEQ ID NO 27
<211> LENGTH: 34
<212> TYPE: PRT
<213> ORGANISM: Rattus norvegicus
```

-continued

```
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 27

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 28
<211> LENGTH: 34
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 28

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 29
<211> LENGTH: 34
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 29

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 30
<211> LENGTH: 34
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 30

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 31
<211> LENGTH: 35
<212> TYPE: PRT
```

```
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 31

Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35

<210> SEQ ID NO 32
<211> LENGTH: 35
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 32

Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35

<210> SEQ ID NO 33
<211> LENGTH: 35
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 33

Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35

<210> SEQ ID NO 34
<211> LENGTH: 35
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 34

Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35
```

```
<210> SEQ ID NO 35
<211> LENGTH: 32
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 35

Lys Lys Lys Lys Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 36
<211> LENGTH: 32
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 36

Lys Lys Lys Lys Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 37
<211> LENGTH: 31
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 37

Arg Arg Arg Ser Gly Arg Gly Gly Gly Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 38
<211> LENGTH: 31
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 38

Arg Arg Arg Ser Gly Arg Gly Ser Gly Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 39
<211> LENGTH: 31
<212> TYPE: PRT
<213> ORGANISM: Homo Sapiens
<220> FEATURE:
```

-continued

```
<221> NAME/KEY: MISC_FEATURE
<222> LOCATION: (1)..(1)
<223> OTHER INFORMATION: Modified by CH3(CH2)16CO
<220> FEATURE:
<221> NAME/KEY: MISC_FEATURE
<222> LOCATION: (31)..(31)
<223> OTHER INFORMATION: Modified by NH2

<400> SEQUENCE: 39

Arg Arg Arg Ser Leu Pro Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 40
<211> LENGTH: 31
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO
<220> FEATURE:
<221> NAME/KEY: MISC_FEATURE
<222> LOCATION: (31)..(31)
<223> OTHER INFORMATION: Modified by NH2

<400> SEQUENCE: 40

Arg Arg Arg Ser Leu Pro Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 41
<211> LENGTH: 32
<212> TYPE: PRT
<213> ORGANISM: Homo Sapiens

<400> SEQUENCE: 41

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 42
<211> LENGTH: 33
<212> TYPE: PRT
<213> ORGANISM: Homo Sapiens

<400> SEQUENCE: 42

Gly Ser Pro Lys Met Val Gln Gly Ser Gly Cys Phe Gly Arg Lys Met
1               5                   10                  15

Asp Arg Ile Ser Ser Ser Ser Gly Leu Gly Cys Lys Val Leu Arg Arg
            20                  25                  30

His

<210> SEQ ID NO 43
<211> LENGTH: 34
<212> TYPE: PRT
<213> ORGANISM: Homo Sapiens

<400> SEQUENCE: 43

Gly Gly Ser Pro Lys Met Val Gln Gly Ser Gly Cys Phe Gly Arg Lys
1               5                   10                  15
```

-continued

```
Met Asp Arg Ile Ser Ser Ser Ser Gly Leu Gly Cys Lys Val Leu Arg
        20                  25                  30

Arg His

<210> SEQ ID NO 44
<211> LENGTH: 35
<212> TYPE: PRT
<213> ORGANISM: Homo Sapiens

<400> SEQUENCE: 44

Gly Gly Gly Ser Pro Lys Met Val Gln Gly Ser Gly Cys Phe Gly Arg
1               5                   10                  15

Lys Met Asp Arg Ile Ser Ser Ser Ser Gly Leu Gly Cys Lys Val Leu
        20                  25                  30

Arg Arg His
        35

<210> SEQ ID NO 45
<211> LENGTH: 36
<212> TYPE: PRT
<213> ORGANISM: Homo Sapiens

<400> SEQUENCE: 45

Lys Gly Gly Gly Ser Pro Lys Met Val Gln Gly Ser Gly Cys Phe Gly
1               5                   10                  15

Arg Lys Met Asp Arg Ile Ser Ser Ser Ser Gly Leu Gly Cys Lys Val
        20                  25                  30

Leu Arg Arg His
        35

<210> SEQ ID NO 46
<211> LENGTH: 37
<212> TYPE: PRT
<213> ORGANISM: Homo Sapiens

<400> SEQUENCE: 46

Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
        20                  25                  30

Val Leu Arg Arg His
        35

<210> SEQ ID NO 47
<211> LENGTH: 38
<212> TYPE: PRT
<213> ORGANISM: Homo Sapiens

<400> SEQUENCE: 47

Lys Lys Lys Gly Gly Gly Ser Pro Lys Met Val Gln Gly Ser Gly Cys
1               5                   10                  15

Phe Gly Arg Lys Met Asp Arg Ile Ser Ser Ser Ser Gly Leu Gly Cys
        20                  25                  30

Lys Val Leu Arg Arg His
        35

<210> SEQ ID NO 48
<211> LENGTH: 39
<212> TYPE: PRT
<213> ORGANISM: Homo Sapiens
```

-continued

<400> SEQUENCE: 48

```
Lys Lys Lys Lys Gly Gly Gly Ser Pro Lys Met Val Gln Gly Ser Gly
1               5                  10                  15

Cys Phe Gly Arg Lys Met Asp Arg Ile Ser Ser Ser Ser Gly Leu Gly
                20                  25                  30

Cys Lys Val Leu Arg Arg His
        35
```

<210> SEQ ID NO 49
<211> LENGTH: 38
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 49

```
Lys Lys Lys Gly Gly Gly Ser Pro Lys Met Val Gln Gly Ser Gly Cys
1               5                  10                  15

Phe Gly Arg Lys Met Asp Arg Ile Ser Ser Ser Ser Gly Leu Gly Cys
                20                  25                  30

Lys Val Leu Arg Arg His
        35
```

<210> SEQ ID NO 50
<211> LENGTH: 38
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 50

```
Lys Lys Lys Gly Gly Gly Ser Pro Lys Met Val Gln Gly Ser Gly Cys
1               5                  10                  15

Phe Gly Arg Lys Met Asp Arg Ile Ser Ser Ser Ser Gly Leu Gly Cys
                20                  25                  30

Lys Val Leu Arg Arg His
        35
```

<210> SEQ ID NO 51
<211> LENGTH: 38
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 51

```
Lys Lys Lys Gly Gly Gly Ser Pro Lys Met Val Gln Gly Ser Gly Cys
1               5                  10                  15

Phe Gly Arg Lys Met Asp Arg Ile Ser Ser Ser Ser Gly Leu Gly Cys
                20                  25                  30

Lys Val Leu Arg Arg His
        35
```

<210> SEQ ID NO 52
<211> LENGTH: 38
<212> TYPE: PRT
<213> ORGANISM: Homo Sapiens -continued

```
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 52

Lys Lys Lys Gly Gly Gly Ser Pro Lys Met Val Gln Gly Ser Gly Cys
1               5                   10                  15

Phe Gly Arg Lys Met Asp Arg Ile Ser Ser Ser Ser Gly Leu Gly Cys
            20                  25                  30

Lys Val Leu Arg Arg His
        35

<210> SEQ ID NO 53
<211> LENGTH: 39
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 53

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His
        35

<210> SEQ ID NO 54
<211> LENGTH: 39
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 54

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His
        35

<210> SEQ ID NO 55
<211> LENGTH: 39
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 55

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His
        35
```

-continued

```
<210> SEQ ID NO 56
<211> LENGTH: 42
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 56

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His Cys Asn Pro
        35                  40

<210> SEQ ID NO 57
<211> LENGTH: 22
<212> TYPE: PRT
<213> ORGANISM: Homo Sapiens

<400> SEQUENCE: 57

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 58
<211> LENGTH: 23
<212> TYPE: PRT
<213> ORGANISM: Homo Sapiens

<400> SEQUENCE: 58

Gly Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 59
<211> LENGTH: 24
<212> TYPE: PRT
<213> ORGANISM: Homo Sapiens

<400> SEQUENCE: 59

Gly Gly Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 60
<211> LENGTH: 25
<212> TYPE: PRT
<213> ORGANISM: Homo Sapiens

<400> SEQUENCE: 60

Gly Gly Gly Gly Leu Ser Lys Gly Cys Phe Gly Leu Lys Leu Asp Arg
1               5                   10                  15

Ile Gly Ser Met Ser Gly Leu Gly Cys
            20                  25

<210> SEQ ID NO 61
```

-continued

```
<211> LENGTH: 26
<212> TYPE: PRT
<213> ORGANISM: Homo Sapiens

<400> SEQUENCE: 61

Lys Gly Gly Gly Gly Leu Ser Lys Gly Cys Phe Gly Leu Lys Leu Asp
1               5                   10                  15

Arg Ile Gly Ser Met Ser Gly Leu Gly Cys
            20                  25

<210> SEQ ID NO 62
<211> LENGTH: 27
<212> TYPE: PRT
<213> ORGANISM: Homo Sapiens

<400> SEQUENCE: 62

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 63
<211> LENGTH: 28
<212> TYPE: PRT
<213> ORGANISM: Homo Sapiens

<400> SEQUENCE: 63

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 64
<211> LENGTH: 29
<212> TYPE: PRT
<213> ORGANISM: Homo Sapiens

<400> SEQUENCE: 64

Lys Lys Lys Lys Gly Gly Gly Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 65
<211> LENGTH: 28
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 65

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 66
<211> LENGTH: 28
<212> TYPE: PRT
<213> ORGANISM: Homo Sapiens
<220> FEATURE:
<221> NAME/KEY: MISC_FEATURE
```

<222> LOCATION: (1)..(1)
<223> OTHER INFORMATION: Modified by CH3(CH2)12CO

<400> SEQUENCE: 66

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 67
<211> LENGTH: 28
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 67

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 68
<211> LENGTH: 28
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 68

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 69
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 69

Lys Lys Lys Lys Gly Gly Gly Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 70
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 70

Lys Lys Lys Lys Gly Gly Gly Gly Leu Ser Lys Gly Cys Phe Gly Leu
1               5                   10                  15

```
Lys Leu Asp Arg Ile Gly Ser Met Ser Gly Leu Gly Cys
            20                  25

<210> SEQ ID NO 71
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 71

Lys Lys Lys Lys Gly Gly Gly Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 72
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 72

Lys Lys Lys Lys Gly Gly Gly Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 73
<211> LENGTH: 33
<212> TYPE: PRT
<213> ORGANISM: Homo Sapiens
<220> FEATURE:
<221> NAME/KEY: MISC_FEATURE
<222> LOCATION: (1)..(2)
<223> OTHER INFORMATION: Modified by CH3(CH2)12CO

<400> SEQUENCE: 73

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 74
<211> LENGTH: 33
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 74

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr
```

```
<210> SEQ ID NO 75
<211> LENGTH: 33
<212> TYPE: PRT
<213> ORGANISM: Mus
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 75

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30

Tyr

<210> SEQ ID NO 76
<211> LENGTH: 33
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 76

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30

Tyr

<210> SEQ ID NO 77
<211> LENGTH: 33
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 77

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30

Tyr

<210> SEQ ID NO 78
<211> LENGTH: 33
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 78

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30
```

Tyr

<210> SEQ ID NO 79
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 79

Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
            20                  25                  30

Val Leu Arg Arg His
        35

<210> SEQ ID NO 80
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 80

Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
            20                  25                  30

Val Leu Arg Arg His
        35

<210> SEQ ID NO 81
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by  CH3(CH2)14CO

<400> SEQUENCE: 81

Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
            20                  25                  30

Val Leu Arg Arg His
        35

<210> SEQ ID NO 82
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 82

Lys Lys Gly Gly Gly Ser Pro Lys Met Val Gln Gly Ser Gly Cys Phe
1               5                   10                  15

-continued

```
Gly Arg Lys Met Asp Arg Ile Ser Ser Ser Ser Gly Leu Gly Cys Lys
            20                  25                  30

Val Leu Arg Arg His
        35
```

```
<210> SEQ ID NO 83
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)10CO

<400> SEQUENCE: 83

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25
```

```
<210> SEQ ID NO 84
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)12CO

<400> SEQUENCE: 84

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25
```

```
<210> SEQ ID NO 85
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)14CO

<400> SEQUENCE: 85

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25
```

```
<210> SEQ ID NO 86
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)16CO

<400> SEQUENCE: 86

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25
```

<210> SEQ ID NO 87
<211> LENGTH: 33
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 87

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 88
<211> LENGTH: 33
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 88

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 89
<211> LENGTH: 33
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 89

Lys Lys Gly Gly Gly Ser Leu Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 90
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 90

Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr

-continued

```
<210> SEQ ID NO 91
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 91

Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr

<210> SEQ ID NO 92
<211> LENGTH: 34
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 92

Lys Lys Lys Gly Gly Gly Ser Leu Arg Arg Ser Ser Cys Phe Gly Gly
1               5                   10                  15

Arg Met Asp Arg Ile Gly Ala Gln Ser Gly Leu Gly Cys Asn Ser Phe
            20                  25                  30

Arg Tyr

<210> SEQ ID NO 93
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 93

Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30

Phe Arg Tyr
        35

<210> SEQ ID NO 94
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 94

Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30
```

-continued

```
Phe Arg Tyr
        35

<210> SEQ ID NO 95
<211> LENGTH: 35
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 95

Lys Lys Lys Lys Gly Gly Gly Ser Leu Arg Arg Ser Ser Cys Phe Gly
1               5                   10                  15

Gly Arg Met Asp Arg Ile Gly Ala Gln Ser Gly Leu Gly Cys Asn Ser
            20                  25                  30

Phe Arg Tyr
        35

<210> SEQ ID NO 96
<211> LENGTH: 33
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 96

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30

Tyr

<210> SEQ ID NO 97
<211> LENGTH: 33
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 97

Lys Lys Gly Gly Gly Ser Leu Arg Arg Ser Ser Cys Phe Gly Gly Arg
1               5                   10                  15

Ile Asp Arg Ile Gly Ala Gln Ser Gly Leu Gly Cys Asn Ser Phe Arg
            20                  25                  30

Tyr

<210> SEQ ID NO 98
<211> LENGTH: 33
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 98

Lys Lys Gly Gly Gly Ser Leu Arg Arg Ser Ser Cys Phe Gly Gly Arg
1               5                   10                  15
```

```
Ile Asp Arg Ile Gly Ala Gln Ser Gly Leu Gly Cys Asn Ser Phe Arg
            20                  25                  30

Tyr

<210> SEQ ID NO 99
<211> LENGTH: 34
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 99

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 100
<211> LENGTH: 34
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 100

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 101
<211> LENGTH: 34
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 101

Lys Lys Lys Gly Gly Gly Ser Leu Arg Arg Ser Ser Cys Phe Gly Gly
1               5                   10                  15

Arg Ile Asp Arg Ile Gly Ala Gln Ser Gly Leu Gly Cys Asn Ser Phe
            20                  25                  30

Arg Tyr

<210> SEQ ID NO 102
<211> LENGTH: 35
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by  CH3(CH2)18CO

<400> SEQUENCE: 102

Lys Lys Lys Lys Gly Gly Gly Ser Leu Arg Arg Ser Ser Cys Phe Gly
```

-continued

```
1               5                   10                  15

Gly Arg Ile Asp Arg Ile Gly Ala Gln Ser Gly Leu Gly Cys Asn Ser
            20                  25                  30

Phe Arg Tyr
        35
```

```
<210> SEQ ID NO 103
<211> LENGTH: 35
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 103
```

```
Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35
```

```
<210> SEQ ID NO 104
<211> LENGTH: 35
<212> TYPE: PRT
<213> ORGANISM: Rattus norvegicus
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 104
```

```
Lys Lys Lys Lys Gly Gly Gly Ser Leu Arg Arg Ser Ser Cys Phe Gly
1               5                   10                  15

Gly Arg Ile Asp Arg Ile Gly Ala Gln Ser Gly Leu Gly Cys Asn Ser
            20                  25                  30

Phe Arg Tyr
        35
```

```
<210> SEQ ID NO 105
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 105
```

```
Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
            20                  25                  30

Val Leu Arg Arg His
        35
```

```
<210> SEQ ID NO 106
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
```

<223> OTHER INFORMATION: Modified by CH3(CH2)20CO

<400> SEQUENCE: 106

Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
            20                  25                  30

Val Leu Arg Arg His
        35

<210> SEQ ID NO 107
<211> LENGTH: 37
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 107

Lys Lys Gly Gly Gly Ser Pro Lys Met Val Gln Gly Ser Gly Cys Phe
1               5                   10                  15

Gly Arg Lys Met Asp Arg Ile Ser Ser Ser Ser Gly Leu Gly Cys Lys
            20                  25                  30

Val Leu Arg Arg His
        35

<210> SEQ ID NO 108
<211> LENGTH: 38
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by  CH3(CH2)18CO

<400> SEQUENCE: 108

Lys Lys Lys Gly Gly Gly Ser Pro Lys Met Val Gln Gly Ser Gly Cys
1               5                   10                  15

Phe Gly Arg Lys Met Asp Arg Ile Ser Ser Ser Ser Gly Leu Gly Cys
            20                  25                  30

Lys Val Leu Arg Arg His
        35

<210> SEQ ID NO 109
<211> LENGTH: 38
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 109

Lys Lys Lys Gly Gly Gly Ser Pro Lys Met Val Gln Gly Ser Gly Cys
1               5                   10                  15

Phe Gly Arg Lys Met Asp Arg Ile Ser Ser Ser Ser Gly Leu Gly Cys
            20                  25                  30

Lys Val Leu Arg Arg His
        35

<210> SEQ ID NO 110
<211> LENGTH: 38

```
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 110

Lys Lys Lys Gly Gly Gly Ser Pro Lys Met Val Gln Gly Ser Gly Cys
1               5                   10                  15

Phe Gly Arg Lys Met Asp Arg Ile Ser Ser Ser Ser Gly Leu Gly Cys
            20                  25                  30

Lys Val Leu Arg Arg His
        35

<210> SEQ ID NO 111
<211> LENGTH: 39
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 111

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His
        35

<210> SEQ ID NO 112
<211> LENGTH: 39
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 112

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His
        35

<210> SEQ ID NO 113
<211> LENGTH: 39
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 113

Lys Lys Lys Lys Gly Gly Gly Ser Pro Lys Met Val Gln Gly Ser Gly
1               5                   10                  15

Cys Phe Gly Arg Lys Met Asp Arg Ile Ser Ser Ser Ser Gly Leu Gly
            20                  25                  30

Cys Lys Val Leu Arg Arg His
```

-continued

35

```
<210> SEQ ID NO 114
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 114

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 115
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 115

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 116
<211> LENGTH: 27
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 116

Lys Lys Gly Gly Gly Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 117
<211> LENGTH: 28
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 117

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 118
<211> LENGTH: 28
<212> TYPE: PRT
<213> ORGANISM: Homo Sapiens
```

```
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 118

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 119
<211> LENGTH: 28
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 119

Lys Lys Lys Gly Gly Gly Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 120
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)18CO

<400> SEQUENCE: 120

Lys Lys Lys Lys Gly Gly Gly Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 121
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)20CO

<400> SEQUENCE: 121

Lys Lys Lys Lys Gly Gly Gly Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 122
<211> LENGTH: 29
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: Modified by CH3(CH2)22CO

<400> SEQUENCE: 122
```

```
Lys Lys Lys Lys Gly Gly Gly Gly Leu Ser Lys Gly Cys Phe Gly Leu
1               5                   10              15

Lys Leu Asp Arg Ile Gly Ser Met Ser Gly Leu Gly Cys
            20                  25

<210> SEQ ID NO 123
<211> LENGTH: 4
<212> TYPE: PRT
<213> ORGANISM: Artificial sequence
<220> FEATURE:
<223> OTHER INFORMATION: Synthetic

<400> SEQUENCE: 123

Lys Gly Gly Gly
1

<210> SEQ ID NO 124
<211> LENGTH: 5
<212> TYPE: PRT
<213> ORGANISM: Artificial sequence
<220> FEATURE:
<223> OTHER INFORMATION: Synthetic

<400> SEQUENCE: 124

Lys Lys Gly Gly Gly
1               5

<210> SEQ ID NO 125
<211> LENGTH: 6
<212> TYPE: PRT
<213> ORGANISM: Artificial sequence
<220> FEATURE:
<223> OTHER INFORMATION: Synthetic

<400> SEQUENCE: 125

Lys Lys Lys Gly Gly Gly
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Lys Lys Lys Lys Gly Gly Gly
1               5

<210> SEQ ID NO 127
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 127

Arg Arg Arg Arg
1

<210> SEQ ID NO 128
<211> LENGTH: 4
<212> TYPE: PRT
<213> ORGANISM: ARTIFICIAL SEQUENCE
<220> FEATURE:
<223> OTHER INFORMATION: SYNTHETIC
```

```
<400> SEQUENCE: 128

Lys Lys Lys Lys
1

<210> SEQ ID NO 129
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 129

Lys Arg Arg Arg
1

<210> SEQ ID NO 130
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 130

Arg Lys Arg Arg
1

<210> SEQ ID NO 131
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 131

Arg Arg Lys Arg
1

<210> SEQ ID NO 132
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 132

Arg Arg Arg Lys
1

<210> SEQ ID NO 133
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 133

Lys Lys Arg Arg
1

<210> SEQ ID NO 134
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 134
```

Arg Lys Lys Arg
1

<210> SEQ ID NO 135
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 135

Arg Arg Lys Lys
1

<210> SEQ ID NO 136
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 136

Lys Arg Arg Lys
1

<210> SEQ ID NO 137
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 137

Lys Lys Lys Arg
1

<210> SEQ ID NO 138
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 138

Arg Lys Lys Lys
1

<210> SEQ ID NO 139
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 139

Lys Arg Lys Lys
1

<210> SEQ ID NO 140
<211> LENGTH: 4
<212> TYPE: PRT
<213> ORGANISM: ARTIFICIAL SEQUENCE
<220> FEATURE:
<223> OTHER INFORMATION: SYNTHETIC

<400> SEQUENCE: 140

-continued

```
Lys Lys Arg Lys
1

<210> SEQ ID NO 141
<211> LENGTH: 4
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Lysine or Arginine

<400> SEQUENCE: 141

Xaa Gly Gly Gly
1

<210> SEQ ID NO 142
<211> LENGTH: 5
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(2)
<223> OTHER INFORMATION: Lysine or Arginine

<400> SEQUENCE: 142

Xaa Xaa Gly Gly Gly
1               5

<210> SEQ ID NO 143
<211> LENGTH: 6
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(3)
<223> OTHER INFORMATION: Lysine or Arginine

<400> SEQUENCE: 143

Xaa Xaa Xaa Gly Gly Gly
1               5

<210> SEQ ID NO 144
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(4)
<223> OTHER INFORMATION: Lysine or Arginine

<400> SEQUENCE: 144

Xaa Xaa Xaa Xaa Gly Gly Gly
1               5

<210> SEQ ID NO 145
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
```

```
<221> NAME/KEY: MISC_FEATURE
<222> LOCATION: (1)..(1)
<223> OTHER INFORMATION: CH3(CH2)10CO

<400> SEQUENCE: 145

Lys Lys Lys Lys Gly Gly Gly
1               5

<210> SEQ ID NO 146
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)12CO

<400> SEQUENCE: 146

Lys Lys Lys Lys Gly Gly Gly
1               5

<210> SEQ ID NO 147
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)14CO

<400> SEQUENCE: 147

Lys Lys Lys Lys Gly Gly Gly
1               5

<210> SEQ ID NO 148
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)16CO

<400> SEQUENCE: 148

Lys Lys Lys Lys Gly Gly Gly
1               5

<210> SEQ ID NO 149
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)10CO

<400> SEQUENCE: 149

Arg Arg Arg Arg Gly Gly Gly
1               5

<210> SEQ ID NO 150
```

```
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)12CO

<400> SEQUENCE: 150

Arg Arg Arg Arg Gly Gly Gly
1               5

<210> SEQ ID NO 151
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)14CO

<400> SEQUENCE: 151

Arg Arg Arg Arg Gly Gly Gly
1               5

<210> SEQ ID NO 152
<211> LENGTH: 7
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)16CO

<400> SEQUENCE: 152

Arg Arg Arg Arg Gly Gly Gly
1               5

<210> SEQ ID NO 153
<211> LENGTH: 5
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)pCO, (p is 10 to 22)

<400> SEQUENCE: 153

Lys Lys Gly Gly Gly
1               5

<210> SEQ ID NO 154
<211> LENGTH: 5
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)10CO

<400> SEQUENCE: 154
```

```
Lys Lys Gly Gly Gly
1               5

<210> SEQ ID NO 155
<211> LENGTH: 5
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)16CO

<400> SEQUENCE: 155

Lys Lys Gly Gly Gly
1               5

<210> SEQ ID NO 156
<211> LENGTH: 6
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)pCO, (p is 10 to 22)

<400> SEQUENCE: 156

Lys Lys Lys Gly Gly Gly
1               5

<210> SEQ ID NO 157
<211> LENGTH: 6
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)10CO

<400> SEQUENCE: 157

Lys Lys Lys Gly Gly Gly
1               5

<210> SEQ ID NO 158
<211> LENGTH: 6
<212> TYPE: PRT
<213> ORGANISM: ARTIFICIAL SEQUENCE
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: CH3(CH2)16CO

<400> SEQUENCE: 158

Lys Lys Lys Gly Gly Gly
1               5

<210> SEQ ID NO 159
<211> LENGTH: 7
<212> TYPE: PRT
<213> ORGANISM: ARTIFICIAL SEQUENCE
<220> FEATURE:
<223> OTHER INFORMATION: SYNTHETIC
```

-continued

```
<220> FEATURE:
<221> NAME/KEY: MISC_FEATURE
<222> LOCATION: (1)..(1)
<223> OTHER INFORMATION: CH3(CH2)pCO, (p is 10 to 22)

<400> SEQUENCE: 159

Lys Lys Lys Lys Gly Gly Gly
1               5
```

NPRA AGONISTS, COMPOSITIONS, AND USES THEREOF

CROSS-REFERENCE TO RELATED APPLICATION

This application is a Continuation-in-part of PCT/US2018/023491, filed on Mar. 21, 2018, published in English, which claims the benefit of U.S. Provisional Application No. 62/475,147, filed on Mar. 22, 2017. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
  a) File name: 61651019002_Sequence_Listing.txt; created May 3, 2023, 58,326 Bytes in size.

BACKGROUND

Increasing cyclic guanosine monophosphate (cGMP) in vivo has many applications in various hypertension, vascular congestion, or heart disease in mammals. Attempts to increase cGMP in vivo to treat various cardiovascular diseases or enhance sexual performance resulted in the use of phosphophodiesterases inhibitors 5, 6, and 9 (phosphophodiesterases are enzymes that break down cGMP) (see, e.g., Keravis T, Lugnier C. Br J Pharmacol. 2012; 165:1288-305) or compounds that increase production of cGMP such as nitroglycerin/nitrates and natriuretic peptides.

Atrial natriuretic peptide (ANP) and brain natriuretic peptide (BNP) act through Natriuretic Receptor A (NPRA) and c-type natriuretic peptide (CNP) acts through Natriuretic Receptor B (NPRB) (see, e.g., Silver M A, Curr. Opin. Nephrol. Hypertens., 2006, vol. 15,14-21; Yoshibayashi M. et al., Eur. J. Endocrinol., 1996, vol. 135, 265-268) to increase intracellular cGMP, which is also reflected to some extent by an increase in blood cGMP. When natriuretic receptor ligands bind to the natriuretic transmembrane receptors, which have an intracellular guanylate cyclase domain, the guanylate cyclase activity is activated, resulting in an increased intracellular cGMP, expression of various physiological activities, and an increase of blood cGMP.

The increase in cGMP has beneficial effects in hypertension and/or vascular fluid congestion, and/or heart disease. Intracellular cGMP is widely known as an intracellular second messenger, which is responsible for mediating extracellular signal (from natriuretic peptide such as ANP, BNP, CNP, urodilantin, and Nitrous Oxide) into intracellular action. This is well-examined in the control of vascular smooth muscles tone. It is generally known that an increase in intracellular cGMP in vascular smooth muscle cells relaxes smooth muscles and decreases blood pressure.

ANP and BNP are known medicinal agents to control blood pressure and heart load in patients with heart disease. Human ANP (hANP) is clinically used as a therapeutic agent for acute cardiac failure in Japan and BNP is clinically used as a therapeutic agent for congestive cardiac failure in the United States. The medicinal use of existing natriuretic peptides is limited by their short half-life and limited activity to provide sufficient cGMP and they are normally administered by continuous intravenous infusion.

ANP, BNP, and CNP are peptides having cyclic structure necessary for their activity that is made possible by the presence of disulfide bonds. ANP is a 28-amino acid peptide produced in and secreted from atrial cells. The peptide shows diuretic action in the kidney, and relaxes and dilates vascular smooth muscles in blood vessels. In addition, ANP antagonizes the actions of the renin-angiotensin-aldosterone system (RAAS) and vasopressin. These actions comprehensively reduce the load on the heart through lowering the blood pressure and body fluid volume. Indeed, the secretion of ANP is promoted with elevation of atrial filling pressure in congestive cardiac failure etc., and ANP alleviates the symptoms of congestive cardiac failure via the above-mentioned actions.

BNP is a 32-amino acid peptide that was first found in the brain but later found to be produced and secreted mainly in cardiomyocytes. The secretion of BNP is increased in cardiac failure patients, and BNP alleviates various symptoms associated with cardiac failure via the above-mentioned actions.

ANP and BNP have various physiological activities besides vasodilating action, blood-pressure, and vascular fluid regulation through diuretic action. For example, the actions of ANP on bacterial infection-induced inflammation and associated failure in the endothelial barrier function have been reported (see, e.g., Xing J., et al., J. appl. Physiol., 2011, 110 (1), 213-224).

There is a need for natriuretic peptides having enhanced half-life and activity. The present disclosure seeks to fulfill this need and provides further related advantages. For example, the present disclosure provides novel compositions with surprisingly enhanced activity as measured by increase in cGMP.

SUMMARY

The present disclosure provides a natriuretic peptide derivative of Formula (I), or a composition comprising a natriuretic peptide derivative of Formula (I):

$$\text{(fatty acyl)}_z\text{-(B)}_x\text{-(G)}_y\text{-NP} \tag{I}$$

wherein:
  z is 1, x is an integer from 2 to 4 and y is 3; or
  z is 0, x is an integer from 0 to 4 and y is an integer from 1 to 3;
  fatty acyl includes from 12 to 24 (e.g., 12 to 18) carbons atoms;
  B is lysine or arginine;
  G is glycine;
  NP is a natriuretic peptide;
  if present, $\text{(fatty acyl)}_z$- is covalently linked to the N-terminus of $\text{(B)}_x$;
  $\text{(fatty acyl)}_z\text{-(B)}_x$— is covalently linked to the N-terminus of $\text{(G)}_y$; and
  $\text{(fatty acyl)}_z\text{-(B)}_x\text{-(G)}_y$- is covalently linked to the N-terminus of NP.

In one embodiment, the natriuretic peptide derivative, or the composition comprising the natriuretic peptide derivative, increases the level of blood cGMP when parenterally administered to a mammal to a level higher than the natriuretic peptide NP when parenterally administered to a mammal at an equivalent dose (e.g., mole/Kg dose, mg/Kg dose, or both mole/Kg and mg/Kg dose). As used herein, because the addition derivative has a lower mole/Kg dose when given at an equal mg/Kg dose, then if an activity is comparable at the same mg/Kg dose, the addition derivative is expected to be more active on the same mole/Kg dose.

NP is typically a parent natriuretic peptide naturally found in living organisms. NP can be selected from human ANP (SEQ ID NO. 1), rodent ANP (SEQ ID NO. 19), human BNP (SEQ ID NO. 41) and human ANP (SEQ ID NO. 57).

In one embodiment, NP is human ANP (SEQ ID NO. 1).

In one embodiment, B is lysine.

The natriuretic peptide derivative, or the composition comprising the natriuretic peptide derivative, according to the disclosure can include a natriuretic peptide derivative of Formula (II):

$$\text{fatty acyl-}(B)_x\text{-}(G)_3\text{-NP} \qquad\qquad (II),$$

wherein:

the fatty acyl has 12 to 24 (e.g., 12 to 18) carbons atoms;

B is lysine or arginine (e.g., B is lysine);

x is 2-4;

G is glycine;

NP is a natriuretic peptide;

fatty acyl- is covalently linked to the N-terminus of $(B)_x$;

fatty acyl-$(B)_x$— is covalently linked to the N-terminus of $(G)_3$; and fatty acyl-$(B)_x$-$(G)_3$- is covalently linked to the N-terminus of NP.

When administered to mammals, the natriuretic peptide derivative, or the composition comprising the natriuretic peptide derivative, typically increases the blood cGMP to a level higher than a corresponding parent NP when administered at an equivalent dose (e.g., mole/Kg dose, mg/Kg dose, or both mole/Kg and mg/Kg dose).

In one embodiment, x is 2. In one embodiment, x is 3. In one embodiment x is 4.

In some embodiments, in fatty acyl-$(B)_x$-$(G)_3$-NP, x=4; NP is optionally selected from SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In some embodiments, in fatty acyl-$(B)_x$-$(G)_3$-NP, x=3; NP is optionally selected from SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In some embodiments, in fatty acyl-$(B)_x$-$(G)_3$-NP, x=2; NP is optionally selected from SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In some embodiments, in fatty acyl-$(B)_x$-$(G)_3$-NP, x=1; NP is optionally selected from anyone of SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In one embodiment, fatty acyl includes 18 carbon atoms.

In one embodiment, $-(B)_x$-$(G)_3$- is selected from -KKGGG- (SEQ ID NO. 124), -KKKGGG-(SEQ ID NO. 125) and -KKKKGGG- (SEQ ID NO. 126).

In one embodiment, the natriuretic peptide derivative is as defined in one of SEQ ID NO. 9, SEQ ID NO. 10, SEQ ID NO. 11, SEQ ID NO. 14, SEQ ID NO. 18, SEQ ID NO. 56, SEQ ID NO. 82, SEQ ID NO. 52, SEQ ID NO. 113, SEQ ID NO. 68, SEQ ID NO. 122, and SEQ ID NO. 72; or the composition comprising the natriuretic peptide derivative includes a natriuretic peptide derivative as defined in one of SEQ ID NO. 9, SEQ ID NO. 10, SEQ ID NO. 11, SEQ ID NO. 14, SEQ ID NO. 18, SEQ ID NO. 56, SEQ ID NO. 82, SEQ ID NO. 52, SEQ ID NO. 113, SEQ ID NO. 68, SEQ ID NO. 122, and SEQ ID NO. 72.

In one embodiment, the natriuretic peptide derivative is as defined in one of SEQ ID NO. 14, SEQ ID NO. 18, SEQ ID NO. 56, SEQ ID NO. 82, SEQ ID NO. 52, SEQ ID NO. 68, SEQ ID NO. 122, and SEQ ID NO. 72; or the composition comprising the natriuretic peptide derivative includes a natriuretic peptide derivative as defined in one of SEQ ID NO. 14, SEQ ID NO. 18, SEQ ID NO. 56, SEQ ID NO. 82, SEQ ID NO. 52, SEQ ID NO. 68, SEQ ID NO. 122, and SEQ ID NO. 72.

In one embodiment, the natriuretic peptide derivative is as defined in one of SEQ ID NO. 93, SEQ ID NO. 94, SEQ ID NO. 95, SEQ ID NO. 102, SEQ ID NO. 103, SEQ ID NO. 104, SEQ ID NO. 111, SEQ ID NO. 112, SEQ ID NO. 113, SEQ ID NO. 120, SEQ ID NO. 121, and SEQ ID NO. 122, or the composition comprising the natriuretic peptide derivative includes a natriuretic peptide derivative as defined in one of SEQ ID NO. 93, SEQ ID NO. 94, SEQ ID NO. 95, SEQ ID NO. 102, SEQ ID NO. 103, SEQ ID NO. 104, SEQ ID NO. 111, SEQ ID NO. 112, SEQ ID NO. 113, SEQ ID NO. 120, SEQ ID NO. 121, and SEQ ID NO. 122.

In one embodiment, the natriuretic peptide derivative is as defined in one of SEQ ID NO. 18, SEQ ID NO. 34, SEQ ID NO. 56, and SEQ ID NO. 72; or the composition comprising the natriuretic peptide derivative includes a natriuretic peptide derivative as defined in one of SEQ ID NO. 18, SEQ ID NO. 34, SEQ ID NO. 56, and SEQ ID NO. 72.

In one embodiment, the natriuretic peptide derivative is as defined in one of SEQ ID NO. 14, SEQ ID NO. 30, SEQ ID NO. 52, and SEQ ID NO. 68; or the composition comprising the natriuretic peptide derivative includes a natriuretic peptide derivative as defined in one of SEQ ID NO. 14, SEQ ID NO. 30, SEQ ID NO. 52, and SEQ ID NO. 68.

In one embodiment, the natriuretic peptide derivative is as defined in one of SEQ ID NO. 10, SEQ ID NO. 30, SEQ ID NO. 52, and SEQ ID NO. 68; or the composition comprising the natriuretic peptide derivative includes a natriuretic peptide derivative as defined in one of SEQ ID NO. 10, SEQ ID NO. 30, SEQ ID NO. 52, and SEQ ID NO. 68.

In one embodiment, the natriuretic peptide derivative is as defined in one of SEQ ID NO. 9, SEQ ID NO. 10, SEQ ID NO. 11, SEQ ID NO. 14, SEQ ID NO. 18, SEQ ID NO. 56, and SEQ ID NO. 72; or the composition comprising the natriuretic peptide derivative includes a natriuretic peptide derivative as defined in one of SEQ ID NO. 9, SEQ ID NO. 10, SEQ ID NO. 11, SEQ ID NO. 14, SEQ ID NO. 18, SEQ ID NO. 56, and SEQ ID NO. 72.

In one embodiments, the natriuretic peptide derivative is as defined in one of SEQ ID NO. 73, SEQ ID NO. 74, SEQ ID NO. 79, SEQ ID NO. 80, SEQ ID NO. 81, SEQ ID NO. 83, SEQ ID NO. 84, and SEQ ID No. 85; or the composition comprising the natriuretic peptide derivative includes a natriuretic peptide derivative as defined in one of SEQ ID NO. 73, SEQ ID NO. 74, SEQ ID NO. 79, SEQ ID NO. 80, SEQ ID NO. 81, SEQ ID NO. 83, SEQ ID NO. 84, and SEQ ID No. 85.

In one embodiment, the natriuretic peptide derivative is as defined in one of SEQ ID NOs. 87 to 122; or the composition comprising the natriuretic peptide derivative includes a natriuretic peptide derivative as defined in one of SEQ ID NOs. 87 to 122.

The natriuretic peptide derivative according to the disclosure, or the composition comprising the natriuretic peptide derivative, can include a natriuretic peptide derivative of Formula (III):

$$(B)_x\text{-}(G)_y\text{-NP} \qquad\qquad (III),$$

wherein:

B is lysine or arginine (e.g., B is lysine);

x is 0-4;

G is glycine;

y is 1-3;

NP is a natriuretic peptide; and $(B)_x(G)_y$- is covalently linked to the N-terminus of NP.

When administered to mammals, $(B)_x$-$(G)_y$-NP, or a composition comprising a natriuretic peptide derivative $(B)_x$-$(G)_y$-NP, can increase the blood cGMP to a level higher than a corresponding parent NP when administered at an equivalent dose (e.g., mole/Kg dose, mg/Kg dose, or both mole/Kg and mg/Kg dose).

In one embodiment, x is 0. In one embodiment, x is 1. In one embodiment, x is 2. In one embodiment, x is 3. In one embodiment, x is 4. In one embodiment, y is 1. In one embodiment, y is 2. In one embodiment, y is 3.

In some embodiments, in $(B)_x$-$(G)_y$-NP, x=0; and y is optionally 1, 2, or 3; NP is optionally selected from SEQ ID NOs. 1, 19, 41, and 57. For example, NP has SEQ ID NO. 1; NP has SEQ ID NO. 19; NP has SEQ ID NO. 41; or SEQ ID NO. 57.

In some embodiments, in $(B)_x$-$(G)_y$-NP, y=3; B is optionally lysine, and x is optionally 1, 2, 3, or 4; NP is optionally selected from SEQ ID NOs. 1, 19, 41, and 57. For example, NP has SEQ ID NO. 1; NP has SEQ ID NO. 19; NP has SEQ ID NO. 41; or SEQ ID NO. 57.

In one embodiment, y is 3.

In one embodiment, $(B)_x$-$(G)_y$- is selected from G-, GG-, GGG-, KGGG- (SEQ ID NO. 123) and KKKKGGG- (SEQ ID NO. 126).

In one embodiment, the natriuretic peptide derivative is as defined in one of SEQ ID NO. 2, SEQ ID NO. 3, SEQ ID NO. 4, SEQ ID NO. 5, SEQ ID NO. 8 and SEQ ID NO. 44; or the composition comprising the natriuretic peptide derivative includes a natriuretic peptide derivative as defined in one of SEQ ID NO. 2, SEQ ID NO. 3, SEQ ID NO. 4, SEQ ID NO. 5, SEQ ID NO. 8 and SEQ ID NO. 44.

The present disclosure further provides a pharmaceutical composition including a natriuretic peptide derivative as defined herein and an excipient.

The pharmaceutical composition can include, consist essentially of, or consist of, one or more natriuretic peptide derivatives according to the disclosure and an excipient.

In one embodiment, the pharmaceutical composition is for parenteral administration at a dose of natriuretic peptide derivatives less than 1.5 mg/Kg of body weight per day, or at a dose of natriuretic peptide derivatives less than 0.3 mg/Kg of body weight per day, to increase cGMP for the treatment of a disease. In some embodiments, the disease is selected from hypertension, vascular congestion, and heart disease. In certain embodiments, the disease is heart disease.

The present disclosure also provides a natriuretic peptide derivative according to the disclosure, or a composition comprising a natriuretic peptide derivative according to the disclosure for use in the treatment of a disease. The disease can be selected from hypertension, vascular congestion, and heart disease. In one embodiment, the disease is heart disease.

In one embodiment, treatment of the disease includes parenterally administering to a patient the natriuretic peptide derivative according to the disclosure, or a composition comprising the natriuretic peptide derivative according to the disclosure, at a dose of less than 1.5 mg/Kg of body weight per day.

The present disclosure further provides a method of treating a disease in a patient, the method including parenterally administering to the patient a natriuretic peptide derivative according to the disclosure, or a composition comprising a natriuretic peptide derivative according to the disclosure.

The method can include parenterally administering a pharmaceutical composition including, consisting essentially of, or consisting of, one or more natriuretic peptide derivatives according to the disclosure.

The natriuretic peptide derivative, or the composition comprising a natriuretic peptide derivative, can be administered parenterally at a dose of less than 1.5 mg/Kg of body weight per day, or at a dose of less than 0.3 mg/Kg of body weight per day to increase blood cGMP in the patient. In some embodiments, the disease is selected from hypertension, vascular congestion, and heart disease. In certain embodiments, the disease is heart disease.

The present disclosure further provides a method of increasing blood cGMP in a patient, the method including parenterally administering to the patient in need thereof a natriuretic peptide derivative according to the disclosure, or a composition comprising a natriuretic peptide derivative according to the disclosure.

The natriuretic peptide derivative, or the composition comprising the natriuretic peptide derivative, can be administered parenterally at a dose of less than 1.5 mg/Kg of body weight per day, or at a dose of less than 0.3 mg/Kg of body weight per day.

The present disclosure also provides use of a natriuretic peptide derivative according to the disclosure, or a composition comprising a natriuretic peptide derivative according to the disclosure, for the manufacture of a medicament for treating a disease. The disease can be selected from hypertension, vascular congestion, and heart disease.

DETAILED DESCRIPTION

The present disclosure relates to natriuretic peptide derivatives, or compositions thereof, having unexpectedly superior ability to increase blood cGMP and/or intracellular cGMP in vivo compared to native peptide such as atrial natriuretic peptide (ANP) or brain type natriuretic peptide (BNP) or C-type natriuretic peptide (CNP). As described above, ANP, BNP, and CNP are peptides having cyclic structure necessary for their activity that is made possible by the presence of disulfide bonds. The natriuretic peptide derivatives of the present disclosure can also have intramolecular disulfide bonds (between two cysteine residues), resulting in a cyclic structure. The intramolecular disulfide bonds can form in dilute solution spontaneously or with a suitable oxidizing agent. The intramolecular disulfide bridge formation can be confirmed by HPLC/MS analysis.

As used herein, the addition derivative or expansion derivative refers to a peptide derivative where the main backbone amino acid sequence for a peptide remains the same, but the addition of extra functional groups and/or amino acid to the main amino acid sequence using one or more reactive moieties in the main amino acid sequence provides the addition derivative or the expansion derivative. The addition derivative or expansion derivative is different from a truncation and/or substitution peptide derivative where one or more amino acids in the main backbone amino acid sequence of the peptide have been removed and/or replaced by different functional groups and/or amino acids, respectively.

It is believed that alteration of amino acid sequence of peptides can have unpredictable consequences on their biological activity, and alterations that preserve peptide activity is not obvious and unpredictable. The present disclosure describes specific structural alterations of naturally occurring natriuretic peptide (NP). As used herein, naturally occurring natriuretic peptide is referred to throughout as the "parent peptide" or "parent NP," non-limiting examples of which are SEQ. IDs 1 (human ANP), 19 (rodent ANP), 41 (human BNP), and 57 (Human CNP). Briefly, specific alterations of parent NP resulted in surprisingly unexpected enhancement or increased potency compared to the parent NP in vivo as measured by blood cGMP response, while other alterations resulted in loss of activity.

As used herein, the term "potency" refers to an increase in blood cGMP immediately (0-2 hours) after bolus administration relative to the parent native peptide at equal dose.

As used herein, the term "apparent receptor depletion" is synonymous with "receptor depletion" and refers to the loss of the ability of the peptide to have "sustained effect" seen as elevated blood cGMP at a later time (i.e. 6 hours and later).

As used herein, the term "sustained effect" is synonymous with "sustained elevation of cGMP" and refers to the ability of natriuretic peptide to maintain an elevated level of blood cGMP for at least 6 hours after single bolus administration of the peptide.

As used herein, the term "consisting essentially of" or "consists essentially of" refers to a composition including the recited components as well as other components, provided that the other components do not materially affect the essential characteristics of the composition (e.g., bioavailability, pharmacokinetics, toxicity, and/or induce suppression of the activity of the active ingredient).

As used herein, when describing a dimension, measurement, duration, amount, etc., the term "about" indicates a possible difference of +/−5%.

As used herein, the term "fatty acyl" refers to any acyl group derived from fatty acids including saturated and unsaturated fatty acids. For example, typical fatty acyl group derived from unsaturated fatty acids has formula $H_{2a-b}(C)_a(O)$— where "a" can be from 12 to 24 (e.g., 14 to 24, 16 to 24, 18 to 24, 20 to 24, 22 to 24, 12 to 22, 12 to 20, 12 to 18, 12 to 16, 12 to 14, 12, 14, 16, 18, 20, 22, or 24), and "b" can be 1, 3, 5, or 7 (e.g., 1, 3, or 5; 1 or 3; or 1). This formula represent fatty acyl derived from saturated branched and unbranched fatty acids and fatty acid with unsaturation level from none (i.e. b=1) to 3 (i.e. b is 3 when the fatty acid carbon chain includes one double bond, b is 5 when the fatty acid carbon chain includes two double bonds, and b is 7 when the fatty acid carbon chain includes three double bonds). For instance, the natriuretic peptide derivative of Formula (I) can have formula $H_{2a-b}(C)_a(O)$—$(B)_x(G)_3$-NP where "a" is from 12 to 24 and "b" can be 1, 3, 5, or 7. In some embodiments, typical fatty acyl group derived from saturated fatty acids has formula $CH_3(CH_2)_nC(O)$— comprising from 12 to 24 carbon atoms (i.e. when n is an integer from 10 to 22). As an example, the natriuretic peptide derivative of Formula (I) can be of formula $CH_3(CH_2)_nC(O)$—$(B)_x$-$(G)_3$-NP where n is from 10 to 22 (e.g., 12 to 22, 14 to 22, 16 to 22, 18 to 22, 20 to 22, 10 to 20, 10 to 18, 10 to 16, 10 to 14, 10 to 12, 10, 12, 14, 16, 18, 20, or 22). In some embodiments, n is 10 to 14, 12 to 16, 14 to 18, 16 to 20, 18 to 22, or 14 to 16. In some embodiments, fatty acyl includes 12 or 18 carbon atoms (i.e. n is 10 or 16). In certain embodiments, fatty acyl includes 14 or 20 carbon atoms (i.e. n is 12 or 18). In certain embodiments, fatty acyl includes 16 or 22 carbon atoms (i.e. n is 14 or 20). In certain embodiment, fatty acyl includes 18 or 24 carbon atoms (i.e. n is 16 or 22).

In the present specification, the letters in all the disclosed sequences represent conventional single letter amino acid codes for naturally occurring amino acids, where capitalized codes indicate L amino acids and the lower case letters indicate D-amino acids. For instance, glycine can be represented by G, lysine can be represented by K and arginine can be represented by R.

By using allometric scaling at exponent of 0.7 (i.e., dose in other species=mice dose/((mouse weight/weight of average other species)$^{0.7}$)), the 15 mg/Kg in mice is equivalent to about 7.5 mg/Kg rat dose, about 2.5 mg/Kg dog dose, and 1.5 mg/Kg human dose. As used herein, the 15 mg/Kg in mice dose as presented in the relevant data examples, is understood as equivalent to about 7.5 mg/Kg rat dose, which is equivalent to about 2.5 mg/Kg dog dose, which is equivalent to about 1.5 mg/Kg human dose. The 1.5 mg/Kg and the 0.3 mg/Kg dose in the Summary and Claims are interpreted as human dose unless otherwise indicated.

Compositions

The present disclosure provides a natriuretic peptide derivative of Formula (I), or compositions thereof, as defined herein.

In one embodiment, in Formula (I) z is 1, x is 3 or 4 and y is 3, and B is lysine. In Formula (I), NP can be human ANP (SEQ ID NO. 1). In Formula (I), fatty acyl can comprise 12, 18, 20, 22 or 24 carbon atoms.

The present disclosure provides a natriuretic peptide derivative of Formula (II) as defined herein.

In one embodiment, in Formula (II) x is 2, 3 or 4 and B is lysine. In Formula (II), NP can be human ANP (SEQ ID NO. 1). In Formula (II), fatty acyl can comprise 12 or 18 carbon atoms. Alternatively, fatty acyl can comprise from 14 or 18 carbon atoms, from 16 to 18 carbon atoms, or from 20 or 24 carbon atoms.

In one embodiment, the natriuretic peptide derivative is a cGMP-enhancing derivative of natriuretic peptide of Formula fatty acyl-$(B)_x$-$(G)_3$-NP, wherein:

the fatty acyl has 12 to 24 (e.g., 12 to 18) carbons atoms;

B is lysine or arginine (e.g., B is lysine);

x is 2-4;

G is glycine;

NP is the parent natriuretic peptide naturally found in living organism;

fatty acyl- is covalently linked to the N-terminus of $(B)_x$;

fatty acyl-$(B)_x$— is covalently linked to the N-terminus of $(G)_3$;

fatty acyl-$(B)_x$-$(G)_3$- is covalently linked to the N-terminus of NP; and when administered to mammals, the natriuretic peptide derivative increases the blood cGMP to a level higher than a corresponding parent NP when administered at an equivalent dose (e.g., mole/Kg dose, mg/Kg dose, or both mole/Kg and mg/Kg dose).

In some embodiments, in Formula fatty acyl-$(B)_x$-$(G)_3$-NP, x=4; NP is optionally selected from SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In some embodiments, in Formula fatty acyl-$(B)_x$-$(G)_3$-NP, x=3; NP is optionally selected from SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In some embodiments, in Formula fatty acyl-$(B)_x$-$(G)_3$-NP, x=2; NP is optionally selected from SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

In some embodiments, in Formula fatty acyl-$(B)_x$-$(G)_3$-NP, x=1; NP is optionally selected from anyone of SEQ ID NOs. 1, 19, 41, and 57. For example, in some embodiments, B is lysine and NP is SEQ ID NO. 1; B is lysine and NP is SEQ ID NO. 19; B is lysine and NP is SEQ ID NO. 41; and/or B is lysine and NP is SEQ ID NO. 57.

The present disclosure provides a natriuretic peptide derivative of Formula (III) as defined herein.

In one embodiment, in Formula (III), x is 0, 1, 2, 3 or 4 and B is lysine. For instance, in Formula (III), x can be from 2 to 4, for instance 3. In Formula (III), NP can be human ANP (SEQ ID NO. 1).

In one embodiment, the natriuretic peptide derivative is a cGMP-enhancing derivative of natriuretic peptide of Formula $(B)_x$-$(G)_y$-NP, wherein:

B is lysine or arginine (e.g., B is lysine);

x is 0-4;

G is glycine;

y is 1-3;

NP is a parent natriuretic peptide naturally found in living organism;

$(B)_x$-$(G)_y$- is covalently linked to the N-terminus of NP; and when administered to mammals, $(B)_x$-$(G)_y$-NP increases the blood cGMP to a level higher than a corresponding parent NP when administered at an equivalent dose (e.g., mole/Kg dose, mg/Kg dose, or both mole/Kg and mg/Kg dose).

In some embodiments, in Formula $(B)_x$-$(G)_y$-NP, x=0; and y is optionally 1, 2, or 3; NP is optionally selected from SEQ ID NOs. 1, 19, 41, and 57. For example, NP has SEQ ID NO. 1; NP has SEQ ID NO. 19; NP has SEQ ID NO. 41; or SEQ ID NO. 57.

In some embodiments, in Formula $(B)_x$-$(G)_y$-NP, y=3; B is optionally lysine, and x is optionally 1, 2, 3, or 4; NP is optionally selected from SEQ ID NOs. 1, 19, 41, and 57. For example, NP has SEQ ID NO. 1; NP has SEQ ID NO. 19; NP has SEQ ID NO. 41; or SEQ ID NO. 57.

In some embodiments, when B is lysine or arginine, each "B" in $(B)_x$ can be the same or different. For example, $(B)_x$ can be K, R, RR, KK, KR, RK, RRR, KKK, KRR, RKR, RRK, KKR, KRK, RKK, RRRR (SEQ ID NO. 127), KKKK (SEQ ID NO. 128), KRRR (SEQ ID NO. 129), RKRR (SEQ ID NO. 130), RRKR (SEQ ID NO. 131), RRRK (SEQ ID NO. 132), KKRR (SEQ ID NO. 133), RKKR (SEQ ID NO. 134), RRKK (SEQ ID NO. 135), KRRK (SEQ ID NO. 136), KKKR (SEQ ID NO. 137), RKKK (SEQ ID NO. 138), KRKK (SEQ ID NO. 139), KKRK (SEQ ID NO. 140), KKKR (SEQ ID NO. 137), RRRR (SEQ ID NO. 127), or KKKK (SEQ ID NO. 128).

In some embodiments, the natriuretic peptide derivative according to the disclosure can be a natriuretic peptide derivative as defined in any one of SEQ ID NOs. 2 to 18, 20 to 34, 42 to 56 and 58 to 72.

In some embodiments, the natriuretic peptide derivative according to the disclosure can be a natriuretic peptide derivative as defined in any one of SEQ ID NOs. 73 to 86, 87 to 95, 96 to 104, 105 to 113, and 114 to 122.

In one embodiment, the natriuretic peptide derivative is as defined in one of SEQ ID NO. 9, SEQ ID NO. 10, SEQ ID NO. 11, SEQ ID NO. 14, SEQ ID NO. 18, SEQ ID NO. 56 and SEQ ID NO. 72.

In one embodiment, the natriuretic peptide derivative is as defined in one of SEQ ID NO. 2, SEQ ID NO. 3, SEQ ID NO. 4, SEQ ID NO. 5, SEQ ID NO. 8 and SEQ ID NO 44.

In some embodiments, the cGMP-enhancing derivatives of natriuretic peptide having Formula fatty acyl-$(B)_x$-$(G)_3$-NP or $(B)_x$-$(G)_y$-NP can be generically represented by Formula X-peptide.

In one aspect, provided herein are cGMP-enhancing derivatives of natriuretic peptide having Formula X-peptide, or compositions thereof, wherein the peptide moiety is selected from (a) ANP, (b) BNP, and (c) CNP; and X is selected from G, GG, GGG, BGGG (SEQ ID NO. 141), BBGGG (SEQ ID NO. 142), BBBGGG (SEQ ID NO. 143), and BBBBGGG (SEQ ID NO. 144), attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from GG, GGG, BGGG (SEQ ID NO. 141), BBGGG (SEQ ID NO. 142), BBBGGG (SEQ ID NO. 143), and BBBBGGG (SEQ ID NO. 144), attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from GGG, BGGG (SEQ ID NO. 141), BBGGG (SEQ ID NO. 142), BBBGGG (SEQ ID NO. 143), and BBBBGGG (SEQ ID NO. 144), attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from BGGG (SEQ ID NO. 141), BBGGG (SEQ ID NO. 142), BBBGGG (SEQ ID NO. 143), and BBBBGGG (SEQ ID NO. 144), attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from BBGGG (SEQ ID NO. 142), BBBGGG (SEQ ID NO. 143), and BBBBGGG (SEQ ID NO. 144), attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from BBBGGG (SEQ ID NO. 143) and BBBBGGG (SEQ ID NO. 144), attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is BBBBGGG (SEQ ID NO. 144), attached to the N-terminal of the peptide moiety. In the above-mentioned embodiments for the cGMP enhancing derivatives of natriuretic peptide of Formula X-peptide, the letter G is Glycine and B is Lysine or arginine. In some embodiments, in any of the above-mentioned embodiments for the cGMP enhancing derivatives of natriuretic peptide of Formula X-peptide, the letter G is Glycine and B is Lysine (see, e.g., SEQ ID NOs. 5-8, 21-26, 45-48, and 61-64). The cGMP enhancing derivatives of natriuretic peptide of Formula X-peptide can increase the level of blood cGMP after administration in mammals at a level that is similar or higher than their parent natriuretic peptide (ANP, BNP, or CNP). In some embodiments, the cGMP enhancing derivatives of natriuretic peptide of Formula X-peptide increase the level of blood cGMP after administration in mammals at a level that is higher than their parent natriuretic peptide (ANP, BNP, or CNP). The parent natriuretic peptide ANP, BNP, and CNP can have sequences naturally found in vertebrate animals, or more specifically found in mammalian natriuretic peptide (e.g., SEQ ID NOs. 1, 19, 41, or 57).

In another aspect, provided herein are cGMP enhancing derivatives of natriuretic peptide having Formula X-peptide, or compositions thereof, wherein the peptide moiety is selected from (a) ANP, (b) BNP, and (c) CNP and X is selected from $CH_3(CH_2)_{10}COKKKKGGG$ (SEQ ID NO. 145), $CH_3(CH_2)_{12}COKKKKGGG$ (SEQ ID NO. 146), $CH_3(CH_2)_{14}COKKKKGGG$ (SEQ ID NO. 147), and $CH_3(CH_2)_{16}COKKKKGGG$ (SEQ ID NO. 148) attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from $CH_3(CH_2)_{10}COKKKKGGG$ (SEQ ID NO. 145) and $CH_3(CH_2)_{16}COKKKKGGG$ (SEQ ID NO. 148) attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is $CH_3(CH_2)_{16}COKKKKGGG$ (SEQ ID NO. 148) attached to the N-terminal of the peptide moiety. In the above-mentioned embodiments for the cGMP enhancing derivatives of natriuretic peptide of Formula X-peptide, the letter G is Glycine, K is Lysine, and $CH_3(CH_2)_{[10, 12, 14, or 16]}CO$ groups are standard chemical formula for alkyl carbonyl and subscript [10, 12, 14, or 16] represent the number of $CH_2$ groups in the alkyl chain. The cGMP enhancing derivatives of natriuretic peptide of Formula X-peptide can increase the level of blood cGMP after administration in mammals at a level that is similar or higher than their parent natriuretic peptide (ANP, BNP, or CNP). In some embodiments, the cGMP enhancing derivatives of natriuretic peptide of Formula X-peptide increase the level of blood cGMP after administration in mammals at a level that is higher than their parent natriuretic peptide (ANP, BNP, or CNP). The parent natriuretic peptide ANP, BNP, and CNP can have sequences naturally found in vertebrate animals, or more specifically found in mammalian natriuretic peptide (e.g., SEQ ID NOs. 1, 19, 41, or 57).

In yet another aspect, provided herein are cGMP enhancing derivatives of natriuretic peptide having Formula X-peptide, or compositions thereof, wherein the peptide moiety is selected from (a) ANP, (b) BNP, and (c) CNP and X is selected from $CH_3(CH_2)_{10}CORRRRGGG$ (SEQ ID NO. 149), $CH_3(CH_2)_{12}CORRRRGGG$ (SEQ ID NO. 150), $CH_3(CH_2)_{14}CORRRRGGG$ (SEQ ID NO. 151), and $CH_3(CH_2)_{16}CORRRRGGG$ (SEQ ID NO. 152) attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is selected from $CH_3(CH_2)_{10}CORRRRGGG$ (SEQ ID NO. 149) and $CH_3(CH_2)_{16}CORRRRGGG$ (SEQ ID NO. 152) attached to the N-terminal of the peptide moiety. In some embodiments, in the cGMP enhancing derivatives of natriuretic peptide of Formula X-peptide, the peptide moiety is selected from (a) ANP, (b) BNP, and (c) CNP and X is $CH_3(CH_2)_{16}CORRRRGGG$ (SEQ ID NO. 152) attached to the N-terminal of the peptide moiety. In the above-mentioned embodiments for the cGMP enhancing derivatives of natriuretic peptide of Formula X-peptide, the letter G is Glycine, R is arginine, and the $CH_3(CH_2)_{[10, 12, 14, or 16]}CO$ groups are standard chemical formula for alkyl carbonyl and [10, 12, 14, or 16] represent the number of $CH_2$ groups in the alkyl chain. The cGMP enhancing derivatives of natriuretic peptide of Formula X-peptide can increase the level of blood cGMP after administration in mammals at a level that is similar or higher than their parent natriuretic peptide (ANP, BNP, or CNP). In some embodiments, the cGMP enhancing derivatives of natriuretic peptide of Formula X-peptide increase the level of blood cGMP after administration in mammals at a level that is higher than their parent natriuretic peptide (ANP, BNP, or CNP). The parent natriuretic peptide ANP, BNP, and CNP can have sequences naturally found in vertebrate animals, or more specifically found in mammalian natriuretic peptide (e.g., SEQ ID NOs. 1, 19, 41, or 57).

In some embodiments, provided herein are cGMP enhancing derivatives of natriuretic peptide having Formula X-peptide; or a composition including, consisting essentially of, or consisting of, cGMP enhancing derivatives of natriuretic peptide having Formula X-peptide; wherein the peptide moiety is ANP, BNP, or CNP; and X is GG (G=glycine) attached to the N-terminal of the peptide moiety. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. For example, when the X-peptide is SEQ ID NO. 3, the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As another example, the X-peptide is SEQ ID NO. 21, the X-peptide increases the level of blood cGMP after administration in mammals at level that is similar or higher than its parent natriuretic peptide ANP SLRRSSCFGGRID-RIGAQSGLGCNSFRY (SEQ ID NO. 1). As an example, when the X-peptide is SEQ ID NO. 43, the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As an example, when the X-peptide is SEQ ID NO. 59, the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is G (glycine) attached to the N-terminal of the peptide moiety. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. As an example, when the X-peptide is SEQ ID NO. 2, the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As another example, when the X-peptide is SEQ ID NO. 20, the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As an example, when the X-peptide is SEQ ID NO. 42, the X-peptide increases the level of blood cGMP after administration in mammals at a level that is similar or higher than (e.g., higher than) its parent natriuretic peptide BNP SPKMVQGSGCFGRKMDRIS-SSSGLGCKVLRRH (SEQ ID NO. 41). As an example, when the X-peptide is SEQ ID NO. 58, the X-peptide increases the level of blood cGMP after administration in mammals at a level that is similar or higher than (e.g., higher than) its parent natriuretic peptide CNP GLSKGCFGLKL-DRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is GGG (G=glycine) attached to the N-terminal of the peptide moiety. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. As an example, when the X-peptide is SEQ ID NO. 4, the X-peptide increases the level of blood cGMP after administration in mammals at a level that is similar or higher than (e.g., higher than) its parent natriuretic peptide ANP SLRRSSCFG-GRMDRIGAQSGLGCNSFRY (SEQ ID NO. 1). As an example, when the X-peptide is SEQ ID NO. 22, the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As an example, when the X-peptide is SEQ ID NO. 44, the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As another example, when the X-peptide is SEQ ID NO. 60, the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is KGGG (SEQ ID NO. 123, K=lysine, G=glycine) attached to the N-terminal of the peptide moiety. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. As an example, when the X-peptide is SEQ ID NO. 5, the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As an example, when the X-peptide is SEQ ID NO. 23, the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As an example, when the X-peptide is SEQ ID NO. 45, the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As another example, As an example, when the X-peptide is SEQ ID NO. 61, the X-peptide increases the level of blood cGMP after administration in mammals at a level that is similar or higher than (e.g., higher than) its parent natriuretic peptide CNP GLSKGCFGLKLDRI-GSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is KKGGG (SEQ ID NO. 124, K=lysine, G=glycine) attached to the N-terminal of the peptide moiety. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. As an example, when the X-peptide is SEQ ID NO. 6, the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As an example, when the X-peptide is SEQ ID NO. 24, the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As an example, when the X-peptide is SEQ ID NO. 46, the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As another example, when the X-peptide is SEQ ID NO. 62, the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is KKKGGG (SEQ ID NO. 125, K=lysine, G=glycine) attached to the N-terminal of the peptide moiety. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. As an example, when the X-peptide is SEQ ID NO. 7, the X-peptide increases the level of blood cGMP after administration in mammals at a level that is similar or higher than (e.g., higher than) its parent natriuretic peptide SLRRSS-CFGGRMDRIGAQSGLGCNSFRY (SEQ ID NO. 1). As another example, when the X-peptide is SEQ ID NO. 25, the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As an example, when the X-peptide is SEQ ID NO. 47, the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As yet another example, when the X-peptide is SEQ ID NO. 63, the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is KKKKGGG (SEQ ID NO. 126, K=lysine, G=glycine) attached to the N-terminal of the peptide moiety. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. As an example, when the X-peptide is SEQ ID NO. 8, the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As another example, when the X-peptide is SEQ ID NO. 26, the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As yet another example, when the X-peptide is SEQ ID NO. 48, the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As another example, when the X-peptide is SEQ ID NO. 64, the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is $CH_3(CH_2)_p$COKKGGG (SEQ ID NO. 153, K=lysine, G=glycine, and $CH_3(CH_2)_p$CO represents a standard chemical formula for alkyl carbonyl, where p is 10 to 22 (e.g., or 10 to 16) and represents the number of repeating $CH_2$ groups in the alkyl chain) attached to the N-terminal of the peptide moiety. In some embodiments, the peptide moiety is ANP or BNP. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. In some embodiments, the parent natriuretic peptide ANP is SLRRSSCFGGRMDRIGAQSGLGCNSFRY (SEQ ID NO. 1), and some representative cGMP enhancing derivatives of natriuretic peptide are SEQ ID NOs. 9, 10, 73, and 74. As an example, when the X-peptide is SEQ ID NO. 9 (peptide moiety is ANP and X is $CH_3(CH_2)_{10}$COKKGGG (SEQ ID NO. 154)

attached to the N-terminal of the peptide moiety), the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As an example, when the X-peptide is SEQ ID NO. 10 (peptide moiety is ANP and X is $CH_3(CH_2)_{16}$COKKGGG (SEQ ID NO. 155) attached to the N-terminal of the peptide moiety), the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). In some embodiments, the parent natriuretic peptide ANP is SLRRSSCFGGRIDRIGAQSGLGCNSFRY (SEQ ID NO. 19), and some representative cGMP enhancing derivatives of natriuretic peptide are SEQ ID NOs. 75-78. As an example, when the X-peptide is SEQ ID NO. 75 (peptide moiety is ANP and X is $CH_3(CH_2)_{10}$COKKGGG (SEQ ID NO. 154) attached to the N-terminal of the peptide moiety), the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As another example, when the X-peptide is SEQ ID NO. 78 (peptide moiety is ANP and X is $CH_3(CH_2)_{16}$ COKKGGG (SEQ ID NO. 155) attached to the N-terminal of the peptide moiety), the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). In some embodiments, the parent natriuretic peptide BNP is SPKMVQGSGCFGRKMDRISSSSGLGCKVLRRH (SEQ ID NO. 41), and some representative cGMP enhancing derivatives of natriuretic peptide are SEQ ID NOs. 79-82. As an example, when the X-peptide is SEQ ID NO. 79 (peptide moiety is BNP and X is $CH_3(CH_2)_{10}$COKKGGG (SEQ ID NO. 154) attached to the N-terminal of the peptide moiety), the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As another example, when the X-peptide is SEQ ID NO. 82 (peptide moiety is BNP and X is $CH_3$ $(CH_2)_{16}$COKKGGG (SEQ ID NO. 155) attached to the N-terminal of the peptide moiety), the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is $CH_3(CH_2)_p$ COKKKGGG (SEQ ID NO. 156, K=lysine, G=glycine, $CH_3(CH_2)_p$CO groups is a standard chemical formula for alkyl carbonyl, where p is 10 to 22 (e.g., or 10 to 16) and represents the number of repeating $CH_2$ groups in the alkyl chain) attached to the N-terminal of the peptide moiety. In some embodiments, the peptide moiety is ANP or BNP. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. In some embodiments, the parent natriuretic peptide is CNP having the sequence GLSKGCFGLKLDRIGSMSGLGC (SEQ ID NO. 57), and some representative cGMP enhancing derivatives of natriuretic peptide are SEQ ID NOs. 83-85. As an example, when the X-peptide is SEQ ID NO. 83 (peptide moiety is CNP, and X is $CH_3(CH_2)_{10}COKKKGGG$ (SEQ ID NO. 157) attached to the N-terminal of the peptide moiety), the X-peptide increases the level of blood cGMP after administration in mammals at a level that is similar or higher than (e.g., higher than) its parent natriuretic peptide CNP GLSKGCFGLKL-DRIGSMSGLGC (SEQ ID NO. 57). As another example, when the X-peptide is SEQ ID NO. 85 (peptide moiety is CNP and X is $CH_3(CH_2)_{16}COKKKGGG$ (SEQ ID NO. 158) attached to the N-terminal of the peptide moiety), the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57). In some embodiments, the parent natriuretic peptide is ANP having the sequence SLRRSSCFGGRMDRI-GAQSGLGCNSFRY (SEQ ID NO. 1), and some representative cGMP enhancing derivatives of natriuretic peptide are SEQ ID NOs. 11-14. As an example, when the X-peptide is SEQ ID NO. 11 (peptide moiety is ANP and X is $CH_3(CH_2)_{10}COKKKGGG$ (SEQ ID NO. 157) attached to the N-terminal of the peptide moiety), the X-peptide increases the level of blood cGMP after administration in mammals at a level that is similar or higher than (e.g., higher than) its parent natriuretic peptide ANP SLRRSSCFGGRMDRI-GAQSGLGCNSFRY (SEQ ID NO. 1). As an example, when the X-peptide is SEQ ID NO. 14 (peptide moiety is ANP and X is $CH_3(CH_2)_{16}COKKKGGG$ (SEQ ID NO. 158) attached to the N-terminal of the peptide moiety), the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). In some embodiments, the parent natriuretic peptide is ANP having the sequence SLRRSSCFGGRIDRI-GAQSGLGCNSFRY (SEQ ID NO. 19), and some representative cGMP enhancing derivatives of natriuretic peptide are SEQ ID NOs. 27-30. As an example, when the X-peptide is SEQ ID NO. 27 (peptide moiety is ANP and X is $CH_3(CH_2)_{10}COKKKGGG$ (SEQ ID NO. 157) attached to the N-terminal of the peptide moiety), the X-peptide increases the level of blood cGMP after administration in mammals at a level that is similar or higher than (e.g., higher than) its parent natriuretic peptide ANP SLRRSSCFGGRID-RIGAQSGLGCNSFRY (SEQ ID NO. 19). As an example, when the X-peptide is SEQ ID NO. 30 (peptide moiety is ANP and X is $CH_3(CH_2)_{16}COKKKGGG$ (SEQ ID NO. 158) attached to the N-terminal of the peptide moiety), the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). In some embodiments, the parent natriuretic peptide is BNP having sequence SPKMVQGSGCFGRKMDRIS-SSSGLGCKVLRRH (SEQ ID NO. 41), and some representative cGMP enhancing derivatives of natriuretic peptide are SEQ ID NOs. 49-52. As an example, when the X-peptide is SEQ ID NO. 49 (peptide moiety is BNP and X is $CH_3(CH_2)_{10}COKKKGGG$ (SEQ ID NO. 157) attached to the N-terminal of the peptide moiety), the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As an example, when the X-peptide is SEQ ID NO. 52 (peptide moiety is BNP and X is $CH_3(CH_2)_{16}COKKKGGG$ (SEQ ID NO. 158) attached to the N-terminal of the peptide moiety), the X-peptide increases the level of blood cGMP after administration in mammals at a level that is similar or higher than (e.g., higher than) its parent natriuretic peptide BNP SPKMVQGSGCFGRKMDRIS-SSSGLGCKVLRRH (SEQ ID NO. 41). In some embodiments, the parent natriuretic peptide is CNP having sequence GLSKGCFGLKLDRIGSMSGLGC (SEQ ID NO. 57), and some representative cGMP enhancing derivatives of natriuretic peptide are SEQ ID NOs. 65-68. As an example, when the X-peptide is SEQ ID NO. 65 (peptide moiety is CNP and X is $CH_3(CH_2)_{10}COKKKGGG$ (SEQ ID NO. 157) attached to the N-terminal of the peptide moiety), the X-peptide increases the level of blood cGMP after administration in mammals at a level that is similar or higher than (e.g., higher than) its parent natriuretic peptide CNP GLSKGCFGLKL-DRIGSMSGLGC (SEQ ID NO. 57). As an example, when the X-peptide is SEQ ID NO. 68 (peptide moiety is CNP and X is $CH_3(CH_2)_{16}COKKKGGG$ (SEQ ID NO. 158) attached to the N-terminal of the peptide moiety), the X-peptide increases the level of blood cGMP after administration in mammals at a level that is similar or higher than (e.g., higher than) its parent natriuretic peptide CNP GLSKGCFGLKL-DRIGSMSGLGC (SEQ ID NO. 57).

In some embodiments, provided herein are cGMP enhancing derivatives of natriuretic peptide having a formula X-peptide; or a composition including, consisting essentially of, or consisting of, cGMP enhancing derivatives of natriuretic peptide having a formula X-peptide; wherein the peptide moiety is ANP, BNP, or CNP; and X is $CH_3(CH_2)_p$ COKKKKGGG (SEQ ID NO. 159) (K=lysine, G=glycine, $CH_3(CH_2)_pCO$ groups is a standard chemical formula for alkyl carbonyl, where p is 10 to 22 (e.g., or 10 to 16) and represents the number of repeating $CH_2$ groups in the alkyl chain) attached to the N-terminal of the peptide moiety. In some embodiments, the peptide moiety is ANP or BNP. In some embodiments, the peptide moiety is ANP. In some embodiments, the peptide moiety is BNP. In some embodiments, the peptide moiety is CNP. The X-peptide can increase the level of blood cGMP after administration in mammals at a level that is similar or higher than (e.g., higher than) its parent natriuretic peptide. In some embodiments, the parent natriuretic peptide is ANP having the sequence SLRRSSCFGGRMDRIGAQSGLGCNSFRY (SEQ ID NO. 1), and some representative cGMP enhancing derivatives of natriuretic peptide are SEQ ID NOs. 15-18. As an example, when the X-peptide is SEQ ID NO. 15 (peptide moiety is ANP and X is $CH_3(CH_2)_{10}COKKKKGGG$ (SEQ ID NO. 145) attached to the N-terminal of the peptide moiety), the X-peptide increases the level of blood cGMP after administration in mammals at a level that is similar or higher than (e.g., higher than) its parent natriuretic peptide ANP SLRRSSCFGGRMDRIGAQSGLGCNSFRY (SEQ ID NO. 1). As an example, when the X-peptide is SEQ ID NO. 18 (peptide moiety is ANP and X is $CH_3(CH_2)_{16}$ COKKKKGGG (SEQ ID NO. 148) attached to the N-terminal of the peptide moiety), the X-peptide increases the level of blood cGMP after administration in mammals at a level that is similar or higher than (e.g., higher than) its parent natriuretic peptide ANP SLRRSSCFGGRMDRI-GAQSGLGCNSFRY (SEQ ID NO. 1). In some embodiments, the parent natriuretic peptide is ANP having the sequence SLRRSSCFGGRIDRIGAQSGLGCNSFRY (SEQ ID NO. 19), and some representative cGMP enhancing derivatives of natriuretic peptide are SEQ ID NOs. 31-34. As an example, when the X-peptide is SEQ ID NO. 31 (peptide moiety is ANP and X is $CH_3(CH_2)_{10}COKKKKGGG$ (SEQ ID NO. 145) attached to the N-terminal of the peptide moiety), the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). As an example, when the X-peptide is SEQ ID NO. 34 (peptide moiety is ANP and X is $CH_3(CH_2)_{16}COKKKKGGG$ (SEQ ID NO. 148) attached to the N-terminal of the peptide moiety), the X-peptide increases the level of blood cGMP after administration in mammals at a level that is similar or higher than (e.g., higher than) its parent natriuretic peptide ANP SLRRSSCFGGRIDRIGAQSGLGCNSFRY (SEQ ID NO. 19). In some embodiments, the parent natriuretic peptide is BNP having the sequence SPKMVQGSGCFGRKMDRISSSSGLGCKVLRRH (SEQ ID NO. 41), and some representative cGMP enhancing derivatives of natriuretic peptide are SEQ ID NOs. 53-56. As an example, when the X-peptide is SEQ ID NO. 53 (peptide moiety is BNP and X is $CH_3(CH_2)_{10}COKKKKGGG$ (SEQ ID NO. 145) attached to the N-terminal of the peptide moiety), the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). As an example, when the X-peptide is SEQ ID NO. 56 (peptide moiety is BNP and X is $CH_3(CH_2)_{16}COKKKKGGG$ (SEQ ID NO. 148) attached to the N-terminal of the peptide moiety), the X-peptide increases the level of blood cGMP after administration in mammals at a level that is similar or higher than (e.g., higher than) its parent natriuretic peptide BNP SPKMVQGSGCFGRKMDRISSSSGLGCKVLRRH (SEQ ID NO. 41). In some embodiments, the parent natriuretic peptide is CNP having the sequence GLSKGCFGLKLDRIGSMSGLGC (SEQ ID NO. 57), and some representative cGMP enhancing derivatives of natriuretic peptide are SEQ ID NOs. 69-72. As an example, when the X-peptide is SEQ ID NO. 69 (peptide moiety is CNP and X is $CH_3(CH_2)_{10}COKKKKGGG$ (SEQ ID NO. 145) attached to the N-terminal of the peptide moiety), the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57). As an example, when the X-peptide is SEQ ID NO. 72 (peptide moiety is CNP and X is $CH_3(CH_2)_{16}COKKKKGGG$ (SEQ ID NO. 148) attached to the N-terminal of the peptide moiety), the X-peptide increases the level of blood cGMP after administration in mammals at a level that is similar or higher than (e.g., higher than) its parent natriuretic peptide CNP GLSKGCFGLKLDRIGSMSGLGC (SEQ ID NO. 57).

Pharmaceutical Compositions and Methods of Use

The disclosure provides a pharmaceutical composition comprising a natriuretic peptide according to the disclosure and an excipient. The pharmaceutical composition can be a pharmaceutical composition including, consisting essentially of, or consisting of, one or more natriuretic peptide derivatives above and an excipient, for parenteral administration at a dose of natriuretic peptide derivatives less than 1.5 mg/Kg of body weight per day, or at a dose of natriuretic peptide derivatives less than 0.3 mg/Kg of body weight per day, to increase cGMP for the treatment of a disease.

In some embodiments, the dose of natriuretic peptide derivatives is more than 0.0001 mg/Kg of body weight per day. For example, the dose of natriuretic peptide derivatives can be more than 0.0001 mg/Kg and/or less than 1.5 mg/Kg of body weight per day. In some embodiments, the dose of natriuretic peptide derivatives is more than 0.0001 mg/Kg and/or less than 1.0 mg/Kg of body weight per day, or more than 0.0001 mg/Kg and/or less than 0.5 mg/Kg of body weight per day. In some embodiments, the dose of natriuretic peptide derivatives is more than 0.0001 mg/Kg and/or less than 0.3 mg/Kg of body weight per day.

In some embodiments, the disease is selected from hypertension, vascular congestion, and heart disease. In certain embodiments, the disease is heart disease.

In yet a further aspect, the present disclosure features a method of treating a disease in a patient, including, consisting essentially of, or consisting of, parenterally administering to the patient one or more natriuretic peptide derivatives above or a pharmaceutical composition including, consisting essentially of, or consisting of, one or more natriuretic peptide derivatives above, at a dose of natriuretic peptide derivatives of less than 1.5 mg/Kg of body weight per day, or at a dose of natriuretic peptide derivatives of less than 0.3 mg/Kg of body weight per day to increase blood cGMP in the patient. In some embodiments, the disease is selected from hypertension, vascular congestion, and heart disease. In certain embodiments, the disease is heart disease.

In yet a further aspect, the present disclosure features a method of increasing blood cGMP in a patient, including, consisting essentially of, or consisting of, parenterally administering to the patient in need thereof one or more natriuretic derivatives above or a pharmaceutical composition including, consisting essentially of, or consisting of, one or more natriuretic peptide derivatives above, at a dose of natriuretic peptide derivatives less than 1.5 mg/Kg of body weight per day, or at a dose of natriuretic peptide derivatives less than 0.3 mg/Kg of body weight per day.

In yet another aspect, the present disclosure describes pharmaceutical compositions including (consisting essentially of, or consisting of) any of the cGMP enhancing derivatives of natriuretic peptide having Formula X-peptide described above, together with one or more appropriate excipients, for parenteral and/or subcutaneous use at a dose (of cGMP enhancing derivative) of less than 1.5 mg/Kg of body weight per day (e.g., less than 0.3 mg/Kg of body weight per day) to increase cGMP, for example, to increase cGMP in mammals to treat diseases that can be ameliorated by increasing cGMP (e.g., blood cGMP). Methods of treatment of diseases that can be ameliorated by increasing cGMP (e.g., blood cGMP), and/or of increasing cGMP (e.g., blood cGMP) are also provided, including (consisting essentially of, or consisting of) parenteral and/or subcutaneous administration of any of the cGMP enhancing derivatives of natriuretic peptide having Formula X-peptide described above, together with one or more appropriate excipients, at a dose (of cGMP enhancing derivative) of less than 1.5 mg/Kg of body weight per day (e.g., less than 0.3 mg/Kg of body weight per day). In some embodiments, the diseases that can be ameliorated by increasing cGMP (e.g., blood cGMP) include, consisting essentially of, or consisting of, hypertension, vascular congestion, heart disease; and treatment can include, consisting essentially of, or consisting of, parenteral and/or subcutaneous administration of any of the cGMP enhancing derivatives of natriuretic peptide having Formula X-peptide described above, together with one or more appropriate excipients, at a dose (of cGMP enhancing derivative) of less than 1.5 mg/Kg of body weight per day (e.g., less than 0.3 mg/Kg of body weight per day). In some embodiments, the cGMP enhancing derivative of natriuretic peptide having Formula X-peptide in the pharmaceutical composition or used in the treatment methods is selected from SEQ ID NOs. 2-18, 20-35, 37, 38, 42-56, and 58-85 administered at a dose indicated above. In some embodiments, the cGMP enhancing derivative of natriuretic peptide having Formula X-peptide in the pharmaceutical composition or used in the treatment methods is selected from SEQ ID NOs. 2-8, 20-26, 42-48, and 58-64, administered at a dose indicated above. In some embodiments, the cGMP enhancing derivative of natriuretic peptide having Formula X-peptide in the pharmaceutical composition or used in the treatment methods is selected from SEQ ID NOs. 9-18, 27-35, 37, 38, 49-56, and 65-122, administered at a dose indicated above. In some embodiments, the cGMP enhancing derivative of natriuretic peptide having Formula X-peptide in the pharmaceutical composition or used in the treatment methods is selected from SEQ ID NOs. 9, 10, 73-89, 96-98, 105-107, and 114-116, administered at a dose indicated above. In some embodiments, the cGMP enhancing derivative of natriuretic peptide having Formula X-peptide in the pharmaceutical composition or used in the treatment methods is selected from SEQ ID NOs. 9, 75, 79, and 83, administered at a dose indicated above. In some embodiments, the cGMP enhancing derivative of natriuretic peptide having Formula X-peptide in the pharmaceutical composition or used in the treatment methods is selected from SEQ ID NOs. 10, 78, 82, and 86, administered at a dose indicated above. In some embodiments, the cGMP enhancing derivative of natriuretic peptide having Formula X-peptide in the pharmaceutical composition or used in the treatment methods is SEQ ID NO. 10, administered at a dose indicated above. In some embodiments, the cGMP enhancing derivative of natriuretic peptide having Formula X-peptide in the pharmaceutical composition or used in the treatment methods is SEQ ID NO. 78, administered at a dose indicated above. In some embodiments, the cGMP enhancing derivative of natriuretic peptide having Formula X-peptide in the pharmaceutical composition or used in the treatment methods is SEQ ID NO. 82, administered at a dose indicated above. In some embodiments, the cGMP enhancing derivative of natriuretic peptide having Formula X-peptide in the pharmaceutical composition or used in the treatment methods is SEQ ID NO. 86, administered at a dose indicated above. In some embodiments, the cGMP enhancing derivative of natriuretic peptide having Formula X-peptide in the pharmaceutical composition or used in the treatment methods is selected from SEQ ID NOs. 11-14, 27-30, 49-52, 65-68, 90-92, 99-101, 108-110, and 117-119 administered at a dose indicated above. In some embodiments, the cGMP enhancing derivative of natriuretic peptide having Formula X-peptide in the pharmaceutical composition or used in the treatment methods is selected from SEQ ID NOs. 11, 14, 27, 30, 49, 52, 65, and 68, administered at a dose indicated above. In some embodiments, the cGMP enhancing derivative of natriuretic peptide having Formula X-peptide in the pharmaceutical composition or used in the treatment methods is selected from SEQ ID NOs. 96-122, administered at a dose indicated above. In some embodiments, the cGMP enhancing derivative of natriuretic peptide having Formula X-peptide in the pharmaceutical composition or used in the treatment methods is selected from SEQ ID NOs. 102-104, administered at a dose indicated above. In some embodiments, the cGMP enhancing derivative of natriuretic peptide having Formula X-peptide in the pharmaceutical composition or used in the treatment methods is selected from SEQ ID NOs. 11, 27, 49, and 65, administered at a dose indicated above. In some embodiments, the cGMP enhancing derivative of natriuretic peptide having Formula X-peptide in the pharmaceutical composition or used in the treatment methods is SEQ ID NO. 11, administered at a dose indicated above. In some embodiments, the cGMP enhancing derivative of natriuretic peptide having Formula X-peptide in the pharmaceutical composition or used in the treatment methods is SEQ ID NO. 27, administered at a dose indicated above. In some embodiments, the cGMP enhancing derivative of natriuretic peptide having Formula X-peptide in the pharmaceutical composition or used in the treatment methods is SEQ ID NO. 49, administered at a dose indicated above. In some embodiments, the cGMP enhancing derivative of natriuretic peptide having Formula X-peptide in the pharmaceutical composition or used in the treatment methods is SEQ ID NO. 65, administered at a dose indicated above. In some embodiments, the cGMP enhancing derivative of natriuretic peptide having Formula X-peptide in the pharmaceutical composition or used in the treatment methods is selected from SEQ ID NOs. 14, 30, 52, and 68, administered at a dose indicated above. In some embodiments, the cGMP enhancing derivative of natriuretic peptide having Formula X-peptide in the pharmaceutical composition or used in the treatment methods is SEQ ID NO. 14, administered at a dose indicated above. In some embodiments, the cGMP enhancing derivative of natriuretic peptide having Formula X-peptide in the pharmaceutical composition or used in the treatment methods is SEQ ID NO. 30, administered at a dose indicated above. In some embodiments, the cGMP enhancing derivative of natriuretic peptide having Formula X-peptide in the pharmaceutical composition or used in the treatment methods is SEQ ID NO. 52, administered at a dose indicated above. In some embodiments, the cGMP enhancing derivative of natriuretic peptide having Formula X-peptide in the pharmaceutical composition or used in the treatment methods is SEQ ID NO. 68, administered at a dose indicated above. In some embodiments, the cGMP enhancing derivative of natriuretic peptide having Formula X-peptide in the pharmaceutical composition or used in the treatment methods is selected from SEQ ID NOs. 15-18, 31-34, 53-56, 69-72, 93-95, 102-104, 111-113, and 120-122, administered at a dose indicated above. In some embodiments, the cGMP enhancing derivative of natriuretic peptide having Formula X-peptide in the pharmaceutical composition or used in the treatment methods is selected from SEQ ID NOs. 15, 18, 31, 34, 53, 56, 69, and 72, administered at a dose indicated above. In some embodiments, the cGMP enhancing derivative of natriuretic peptide having Formula X-peptide in the pharmaceutical composition or used in the treatment methods is selected from SEQ ID NOs. 15, 31, 53, and 69, administered at a dose indicated above. In some embodiments, the cGMP enhancing derivative of natriuretic peptide having Formula X-peptide in the pharmaceutical composition or used in the treatment methods is SEQ ID NO. 15, administered at a dose indicated above. In some embodiments, the cGMP enhancing derivative of natriuretic peptide having Formula X-peptide in the pharmaceutical composition or used in the treatment methods is SEQ ID NO. 31, administered at a dose indicated above. In some embodiments, the cGMP enhancing derivative of natriuretic peptide having Formula X-peptide in the pharmaceutical composition or used in the treatment methods is SEQ ID NO. 53, administered at a dose indicated above. In some embodiments, the cGMP enhancing derivative of natriuretic peptide having Formula X-peptide in the pharmaceutical composition or used in the treatment methods is SEQ ID NO. 69, administered at a dose indicated above. In some embodiments, the cGMP enhancing derivative of natriuretic peptide having Formula X-peptide in the pharmaceutical composition or used in the treatment methods is selected from SEQ ID NOs. 18, 34, 56, and 72, administered at a dose indicated above. In some embodiments, the cGMP enhancing derivative of natriuretic peptide having Formula X-peptide in the pharmaceutical composition or used in the treatment methods is SEQ ID NO. 18, administered at a dose indicated above. In some embodiments, the cGMP enhancing derivative of natriuretic peptide having Formula X-peptide in the pharmaceutical composition or used in the treatment methods is SEQ ID NO. 34, administered at a dose indicated above. In some embodiments, the cGMP enhancing derivative of natriuretic peptide having Formula X-peptide in the pharmaceutical composition or used in the treatment methods is SEQ ID NO. 56, administered at a dose indicated above. In some embodiments, the cGMP enhancing derivative of natriuretic peptide having Formula X-peptide in the pharmaceutical composition or used in the treatment methods is SEQ ID NO. 72, administered at a dose indicated above.

In some embodiments, the cGMP enhancing derivative of natriuretic peptide having Formula X-peptide in the pharmaceutical composition or used in the treatment methods is selected from SEQ ID NOs. 93, 102, 111, and 120, administered at a dose indicated above. In some embodiments, the cGMP enhancing derivative of natriuretic peptide having Formula X-peptide in the pharmaceutical composition or used in the treatment methods is SEQ ID NO. 93, administered at a dose indicated above. In some embodiments, the cGMP enhancing derivative of natriuretic peptide having Formula X-peptide in the pharmaceutical composition or used in the treatment methods is SEQ ID NO. 102, administered at a dose indicated above. In some embodiments, the cGMP enhancing derivative of natriuretic peptide having Formula X-peptide in the pharmaceutical composition or used in the treatment methods is SEQ ID NO. 111, administered at a dose indicated above. In some embodiments, the cGMP enhancing derivative of natriuretic peptide having Formula X-peptide in the pharmaceutical composition or used in the treatment methods is SEQ ID NO. 120, administered at a dose indicated above.

In some embodiments, the cGMP enhancing derivative of natriuretic peptide having Formula X-peptide in the pharmaceutical composition or used in the treatment methods is selected from SEQ ID NOs. 94, 103, 112, and 121, administered at a dose indicated above. In some embodiments, the cGMP enhancing derivative of natriuretic peptide having Formula X-peptide in the pharmaceutical composition or used in the treatment methods is SEQ ID NO. 94, administered at a dose indicated above. In some embodiments, the cGMP enhancing derivative of natriuretic peptide having Formula X-peptide in the pharmaceutical composition or used in the treatment methods is SEQ ID NO. 103, administered at a dose indicated above. In some embodiments, the cGMP enhancing derivative of natriuretic peptide having Formula X-peptide in the pharmaceutical composition or used in the treatment methods is SEQ ID NO. 112, administered at a dose indicated above. In some embodiments, the cGMP enhancing derivative of natriuretic peptide having Formula X-peptide in the pharmaceutical composition or used in the treatment methods is SEQ ID NO. 121, administered at a dose indicated above.

In some embodiments, the cGMP enhancing derivative of natriuretic peptide having Formula X-peptide in the pharmaceutical composition or used in the treatment methods is selected from SEQ ID NOs. 95, 104, 113, and 122, administered at a dose indicated above. In some embodiments, the cGMP enhancing derivative of natriuretic peptide having Formula X-peptide in the pharmaceutical composition or used in the treatment methods is SEQ ID NO. 95, administered at a dose indicated above. In some embodiments, the cGMP enhancing derivative of natriuretic peptide having Formula X-peptide in the pharmaceutical composition or used in the treatment methods is SEQ ID NO. 104, administered at a dose indicated above. In some embodiments, the cGMP enhancing derivative of natriuretic peptide having Formula X-peptide in the pharmaceutical composition or used in the treatment methods is SEQ ID NO. 113, administered at a dose indicated above. In some embodiments, the cGMP enhancing derivative of natriuretic peptide having Formula X-peptide in the pharmaceutical composition or used in the treatment methods is SEQ ID NO. 122, administered at a dose indicated above.

The following example is included for the purpose of illustrating, not limiting, the described embodiments.

Example

Many possible paths are available to increase cGMP in vivo for therapeutic purposes, such as administering exogenous cGMP or ligands that increase endogenous cGMP production or decrease their degradation. The exogenous ligand can aim to affect many different endogenous targets/receptors, including stimulating nitrous oxide pathway, inhibiting phosphodiesterase that degrade cGMP, or stimulating various natriuretic peptide receptors (NPRA or NPRB).

An investigation was carried out to determine whether prolonged presence of ANP in the blood would have a sustained pharmacodynamic effect, reflected by elevation of cGMP blood concentration, and to determine whether that elevation would be proportional to the level of ANP. The level of blood cGMP relative to ANP was determined. Surprisingly, despite elevated level of ANP at 2 and 8 hours, the level of cGMP did not remain elevated, indicating that long acting formulations of native ANP to maintain blood level of ANP at elevated level may not work as expected. This problem had not been documented in literature and there was no reason to solve this previously unknown problem. There were two possibilities to explain this observation: 1) the detected ANP can be inactive or 2) swamping ANP receptor can result in receptor depletion. To investigate whether swamping of ANP receptors would result in loss of response at a later time point and simultaneously rule out the first possibility, an investigation was carried out to study whether plasma cGMP elevation could be restored after a second administration of fresh and (known-to-be) active ANP. For this study, 4 groups of Balb/c mice (n=3/group; female, 5-6 weeks old; 18-25 g) were used and the cGMP levels at various time points after ANP administration with and without $2^{nd}$ ANP administration were evaluated. A high dose was intentionally used to ensure that if receptor depletion was occurring, it would happen in the first dose and no or minimal response would occur after the second dose. Two subsequent s.c. (subcutaneous) administrations of the ANP formulated in a polymeric excipient (to increase in vivo stability) were evaluated. Blood collections were performed at pre (before dosing; 0 hour), 2 hours, and 8 hours after dosing. The 2 dosing groups received the 2nd dose at 6 hours. Blood (~100 uL/point) samples were collected from the retro-orbital sinus and put into chilled test tubes containing dipotassium EDTA. Blood samples were centrifuged at 13,000 rpm for 10 minutes at 4° C. to separate plasma. The plasma samples were analyzed for cGMP using the cGMP ELISA kit (GE Healthcare Life Sciences, Marlborough, MA) according to manufacturer's protocol. The overall procedure included: 1) measure baseline cGMP before administration; 2) inject ANP and measure maximum response at 2 hours; 3) inject a second ANP at 6 hours and measure the maximum cGMP response at 8 hours to see if further elevation of cGMP would be achieved. If there was further elevation which was at least equal or more than the 2 hour time point, then there was no loss of response and the receptor may not be depleted even at high dose. If the response at 8 hour was less than the 2 hour response, then it was reasonable to assume that receptor depletion was occurring; 4) inject higher dose to see dose response. If no dose response was observed then receptor was depleted or saturated. However, it was known that ANP-receptor complexes were internalized by cells that could lead to depletion if supply of receptor was limited. The level of ANP associated with cGMP was also measured to further confirm receptor depletion was the result of lack of responsiveness if any. The associated level of ANP was measured using an ELISA assay kit (GE Healthcare Life Sciences, Marlborough, MA) according to manufacturer's protocol. The results of this study are presented in Table 1.

The results indicated that when NPRA stimulation was attempted using exogenously administered atrial natriuretic peptide (ANP), the ability of natriuretic peptide to increase cGMIP in vivo appeared to be limited by the apparent receptor depletion upon continuous ligand stimulation at high dose. When mice were given a bolus of ANP (12 mg/Kg; s.c.) the blood cGMP level increased by about 80 pmol/ml above baseline at 2 hours and went back to the baseline (4 pmol/ml) at 8 hours. However, when a $2^{nd}$ bolus of ANP was given at 6 hours the blood cGMP level did not increase by the expected additional 80pmol/ml at 8 hours if no receptor depletion is occurring (see Table 1).

The levels of ANP at 2 hours were average of all groups that received the same dose, since in all cases they received the same treatment up to 2 hours. The 8 hour ANP levels in those groups that received $2^{nd}$ administration matched the sum of 2 hour and 8 hour levels from single administration group.

This novel finding indicated that perhaps NPRA (ANP receptor) could be depleted upon continuous stimulation at high dose of ANP. It is known in the art that receptor depletion/internalization effect can be part of a natural negative feedback mechanism of a biological system. The only known way to alter this system was to increase NPRA receptor expression, which at present would not be possible in non-recombinant organism that required treatment to increase blood cGMP. This prompted investigation of new ligands that were potentially more potent in increasing cGMP and can limit the apparent receptor depletion observed in Table 1. It would be counterintuitive to target receptor that was known to deplete (because expression level is low) upon stimulation due to receptor internalization, however it would be useful to discover a ligand that can slow down receptor internalization/depletion, for example, by altering existing ANP ligand with a modification that could slow down or prevent receptor internalization/depletion while maintaining or enhancing the activity of the ANP ligand. However, alterations of existing ANP peptide have unpredictable and non-obvious outcomes in terms of activity, so the only way to discover potent ligands for increasing blood cGMP with limited apparent receptor internalization effect was to do iterative testing of individual natriuretic peptide alteration in vivo.

Various derivatives of ANP were made and screened for increase in vivo potency while limiting the apparent receptor depletion effects (or perhaps can act on another cGMP enhancing receptors) by looking at the level of blood cGMP at specific time points. Any novel derivatives that were potent (indicated by the 2 hour blood cGMP level) and did not cause receptor internalization (indicated by the 6-hour cGMP level) compared to parent ANP peptide control would qualify as novel potential blood cGMP enhancers. Various

TABLE 1

| Results indicating that there was apparent ANP receptor depletion. | | | |
|---|---|---|---|
| | 0 hr Baseline cGMP level pmol/mL (SEM) ANP level ng/ml (SEM) | 2 hrs. cGMP level pmol/mL (SEM) ANP level ng/ml (SEM) | 8 hrs cGMP level pmol/mL (SEM) ANP level ng/ml (SEM) | Injection timing |
|---|---|---|---|---|
| ANP 6 mg/Kg (s.c; n = 3) | cGMP level: 42.4 (5.6) ANP level: 0.096 (0) | cGMP level: 106.1 (10.3) ANP level: 32.62 (4.92) | cGMP level: 34.9 (3.6) ANP level: 57.51 (65.96) | Single Injection at 0 hour only |
| ANP 6 mg/Kg (s.c; n = 3) | cGMP level: 45.5 (7.0) ANP level: 0.096 (0) | cGMP level: 134.9 (25.5) ANP level: 32.62 (4.92) | cGMP level: 87.6 (3.3) ANP level: 89.15 | Injection at 0 hr and 6 hours |
| ANP 12 mg/Kg (s.c; n = 3) | cGMP level: 45.5 (7.0) ANP level: 0.096 (0) | cGMP level: 122.0 (29.4) ANP level: 67.24 (6.92) | cGMP level: 45.5 (6.0) ANP level: 115.02 (3.98) | Single Injection 0 hour only |
| ANP 12 mg/Kg (s.c; n = 3) | cGMP level: 45.5 (7.0) ANP level: 0.096 (0) | cGMP level: 113.6 (3.1)* ANP level: 67.24 (6.92)* | cGMP level: 70.1 (16.2)* ANP level: 182 (10.2)* | Injection at 0 hour and 6 hours |

*Note that the level of blood cGMP level at 2 hours after administration of a single dose was 113 pmol/ml with corresponding ANP level of 67 ng/ml. However, if there was no receptor depletion one would expect that upon $2^{nd}$ administration at 6 hours the level of cGMP at 8 hours (2 hours after $2^{nd}$ administration) to be much higher than 113 pmol/ml (if not the same), instead, cGMP was much lower. The lower cGMP level indicated receptor depletion, resulting in lack of or limited physiological response as reflected by the measured cGMP levels.

derivatives were made and tested in vivo to determine the level of blood cGMP at 2 hours and 6 hours after subcutaneous administration of 15 mg/Kg in mice (which was allometrically equivalent to human dose of 1.5 mg/Kg) with the goal of finding derivatives that were therapeutically useful for increasing blood cGMP.

Many of the protected amino acid residues useful in synthesizing various derivatives of ANP of this disclosure were commercially available from amino acid suppliers. Furthermore, all the peptides that are the subject of the present disclosure can be synthesized by outside custom peptide providers such as Anaspec, San Jose CA. USA, Polypeptide laboratories, Torrance, CA, or ChemPep Inc, Miami, FL. All the peptides that are the subject of the present disclosure were synthesized according to the design specifications and were made, purified, and processed, according to detailed instructions. Synthesis of peptides of the present disclosure can easily be done by those skilled in the art and preferably via solid phase synthesis. Briefly, a protected amino acid corresponding to the C-terminal of the peptide to be made (by Fmoc or Boc, as known in the art) is first immobilized or conjugated with the resin through the carboxyl group. This is followed by de-protection of alpha amino group to allow subsequent addition of the $2^{nd}$ protected amino acid followed by de-protection of alpha amino group, addition of the $3^{rd}$ protected amino acid followed by de-protection of the $2^{nd}$ amino acid, and so on until the last N-terminal amino acid or fatty acid had been added. The cleavage from the resin, de-protection of amino acid functional groups, and purification are similar to conventional peptide synthesis as known in the art. Purification can be achieved using any of the standard approaches, such as reversed phase high pressure liquid chromatography (RP HPLC) on alkylated silica columns, e.g. $C_4$-$C_{18}$ silica. Such column fractionation is generally accomplished by running linear gradients, e.g., 10-90%, of increasing % organic solvent, e.g., acetonitrile, in aqueous buffer, usually containing a small amount (e.g., 0.1%) of ion pairing agent such as trifluoroacetic acid (TFA) or triethyl amine (TEA). Alternatively, ion exchange HPLC can be employed to separate peptide species on the basis of their charge characteristics. Column fractions are collected, and those containing peptide of the desired/required purity are optionally pooled with the guide of a Tandem Mass spectrometry detector. The peptide is then treated in the established manner to exchange the cleaving acid (e.g., TFA) with a pharmaceutically acceptable acid anion and to allow intramolecular disulfide bridge formation in dilute solution under a suitable oxidizing agent. This intramolecular disulfide bridge formation can be confirmed by HPLC/MS analysis.

For 2-point cGMP evaluation of various derivatives, test samples were dissolved in water (Lonza, Wakersville, MD) before being lyophilized. Prior to use, the lyophilized test sample was dissolved in saline then 15 mg/Kg was injected subcutaneously into female CD-1 mice 6-8 weeks (n=3). Blood samples were collected at 2 and 6 hours with K2EDTA blood collection tube. The collection tube was then centrifuged at 13,000 rpm for 10 minutes at 4° C. to separate plasma. The plasma was analyzed using the cGMP Direct Biotrak EIA (GE Healthcare Life Sciences, Marlborough, MA). Note that by using allometric scaling at exponent of 0.7 [dose in other species=mice dose/((mouse weight/weight of average other species)$^{0.7}$)], the 15 mg/Kg in mice is equivalent to about 7.5 mg/Kg rat dose, about 2.5 mg/Kg dog dose, and 1.5 mg/Kg human dose. For the purpose the present disclosure, the 15 mg/Kg in mice as presented in the relevant data examples, should be understood as equivalent to about 7.5 mg/Kg rat dose, which is equivalent to about 2.5 mg/Kg dog dose, which is equivalent to about 1.5 mg/Kg human dose. Because the mice cGMP response to 15 mg/Kg dose of the newly discovered derivatives (see Table 2) was quite high, it would be prudent to use daily doses that are lower than 15 mg/Kg for mice, 7.5 mg/Kg for rat, 2.5 mg/Kg for dog, and 1.5 mg/Kg for human since any higher dose may result in too much increase in cGMP that can result in too much or even dangerous drop in blood pressure unless formulated in a very slow release delivery system. In fact based on cGMP response it was more preferable to use daily doses that are lower than 5 mg/Kg for mice, 1.5 mg/Kg for rat, 0.5 mg/Kg for dog, and 0.3 mg/Kg for human. Additionally, the level of blood cGMP is preferably between 1.5 to 3-times of the normal baseline level. The blood or plasma cGMP normal baseline level was about 20-50 pmol/ml but could vary slightly depending on the assay kit used to measure the level.

The results are presented in Table 2. Iterative testing and modifications at the C-terminal or changing L-arginine near the N-terminal to D-arginine (SEQ ID NOs. 39 and 40) resulted in loss or diminished of activity. Additionally, changing amino acid at the C-terminal (SEQ TD NOs. 37 and 38) resulted in limited increase in activity. Extending the N-terminal (SEQ TD NOs. 2-8, 44, 42, 60, 58) with various numbers of glycine and basic amino acid unexpectedly resulted in no loss activity compared to ANP. However, various N-terminally extended ANP using glycine, basic amino acid, and addition of fatty acid unexpectedly increased potency (see 2 hour data in Table 2; SEQ ID NOs. 9. 10, 11, 14, 15, 18, 56, 72) and prevented apparent receptor depletion/internalization (see 6 hour data in Table 2; SEQ TD Nos. 15, 18,). Similar results were observed with other natriuretic peptides (extended BNP and CNP; SEQ ID Nos. 56, 72). The modifications with fatty acid without glycine had slightly increased in activity but no significant effect on apparent receptor internalization compared to the ANP control (see 6-hour data in Table 2; SEQ ID NO. 35).

TABLE 2

| Potency of (2 h cGMP) and Receptor Depletion by (6 h cGMP) various peptides. | | |
| --- | --- | --- |
| | | In vivo blood cGMP (pmol/ml) minus baseline (30 pmol/ml; n = 12) in mice (n = 3) |
| Seq. ID | Peptide Sequence | 2 hour (SEM) | 6 hour (SEM) |
| None | None [30.3 pmol/ml - baseline is 30.3 pmol/mL (SEM 2.2; n = 12)] | 0 (2.2) | 0 (2.2) |

TABLE 2-continued

Potency of (2 h cGMP) and Receptor Depletion by (6 h cGMP) various peptides.

| Seq. ID | Peptide Sequence | In vivo blood cGMP (pmol/ml) minus baseline (30 pmol/ml; n = 12) in mice (n = 3) | |
|---|---|---|---|
| | | 2 hour (SEM) | 6 hour (SEM) |
| 1) ANP | SLRRSSCFGGRM DRIGAQSGLGCNSFRY | 37.86 (24.54) | −2.44 (17.16) |
| 2) G-ANP | GSLRRSSCFGGRMDRIGAQSGLGCNSFRY | 44.08 (18.37) | −13.85 (4.76) |
| 3) GG-ANP | GGSLRRSSCFGGRMDRIGAQSGLGCNSFRY | 46.79 (31.36) | 0.16 (14.42) |
| 4) GGG-ANP | GGGSLRRSSCFGGRMDRIGAQSGLGCNSFRY | 41.66 (23.27) | −11.79 (2.0) |
| 5) KGGG-ANP | KGGGSLRRSSCFGGRMDRIGAQSGLGCNSFRY | 59.96 (45.75) | 44.34 (34.71) |
| 6) KKGGG-ANP | KKGGGSLRRSSCFGGRMDRIGAQSGLGCNSFRY | 28.6 (25.15) | −4.81 (4.37) |
| 7) KKKGGG-ANP | KKKGGGSLRRSSCFGGRMDRIGAQSGLGCNSFRY | 23.40 (16.18) | −1.19 (4.36) |
| 8) KKKKGGG-ANP | KKKKGGGSLRRSSCFGGRMDRIGAQSGLGCNSFRY | 53.00 (32.17) | 15.25 (12.73) |
| 35) C18-KKKK-ANP | $CH_3(CH_2)_{16}CO-$KKKKSLRRSSCFGGRMDRIGAQSGLGCNSFRY | 45.00 (17.17) | 12.79 (6.65) |
| 36) C18-KKKK-ANP(der) | $CH_3(CH_2)_{16}CO-$KKKKSLRRSSCFGGRMDRIGAQSGLGCNSFrY | inactive | inactive |
| 9) C12KKGGG-ANP | $CH_3(CH_2)_{10}CO-$KKGGGSLRRSSCFGGRMDRIGAQSGLGCNSFRY | 163.62 (53.29) | 4.78 (6.18) |
| 10) C18KKGGG-ANP | $CH_3(CH_2)_{16}CO-$KKGGGSLRRSSCFGGRMDRIGAQSGLGCNSFRY | 183.12 (53.29) | 14.78 (6.18) |
| 11) C12KKKGG-ANP | $CH_3(CH_2)_{10}CO-$KKKGGGSLRRSSCFGGRMDRIGAQSGLGCNSFRY | 136.16 (38.48) | 10.28 (5.58) |
| 14) C18KKKGG-ANP | $CH_3(CH_2)_{16}CO-$KKKGGGSLRRSSCFGGRMDRIGAQSGLGCNSFRY | 574.25 (72.22) | 255.75 (9.35) |
| 15) C12KKKKGGG-ANP | $CH_3(CH_2)_{10}CO-$KKKKGGGSLRRSSCFGGRMDRIGAQSGLGCNSFRY | 60.52 (25.29) | 3.36 (11.04) |
| 18) C18KKKKGGG-ANP | $CH_3(CH_2)_{16}CO-$KKKKGGGSLRRSSCFGGRMDRIGAQSGLGCNSFRY | 355.17 (77.44) | 231.65 (64.45) |
| 37) C18-RRR-ANP(der) | $CH_3(CH_2)_{16}CO-$RRR-SGRGGGCFGGRMDRIGAQSGLG CNSFRY | 45.61 (30.45) | 10.16 (6.53) |
| 38) C18-RRR-ANP(der) | $CH_3(CH_2)_{16}CO-$RRR-SGRGSGCFGGRMDRIGAQSGLG CNSFRY | 33.56 (13.03) | 7.97 (6.01) |

TABLE 2-continued

Potency of (2 h cGMP) and Receptor Depletion by (6 h cGMP) various peptides.

| Seq. ID | Peptide Sequence | In vivo blood cGMP (pmol/ml) minus baseline (30 pmol/ml; n = 12) in mice (n = 3) | |
|---|---|---|---|
| | | 2 hour (SEM) | 6 hour (SEM) |
| 39) C18-RRR-ANP(der) | $CH_3(CH_2)_{16}$CO-RRR-<u>SLPRSS</u>CFGGRMDRIGAQSGLG CNSFRY-$NH_2$ | inactive | inactive |
| 40) C18-RRR-ANP(der) | $CH_3(CH_2)_{16}$CO-RRR-<u>SLPRSS</u>CFGGRMDRIGAQSGLG CNSFrY-$NH_2$ | inactive | inactive |
| 94) C22-KKKKGG G-ANP | $CH_3(CH_2)_{20}$CO KKKKGGGSLRRSSCFGGRMDRIGAQSGLGCNSF RY | 263.8 (73.74) | 255.4 (35.53) |
| 95) C24-KKKKGG G-ANP | $CH_3(CH_2)_{22}$CO KKKKGGGSLRRSSCFGGRMDRIGAQSGLGCNSF RY | 260.8 (76.92) | 245.6 (16.34) |
| 41) BNP | SPKMVQGSGCFGRKMDRISSSSGLGCKVLRRH | 49.77 (19.06) | 8.20 (7.80) |
| 56) C18KKKK GGG-BNP | $CH_3(CH_2)_{16}$COKKKKGGGSPKMVQGSGCFGRKMDRI SSSSGLGCKVLRRH | 479.02 (96.56) | 321.23 (46.78) |
| 44) GGG-BNP | GGGSPKMVQGSGCFGRKMDRISSSSGLGCKVLRRH | 66.59 (4.18) | −5.01 (9.18) |
| 42) G-BNP | GSPKMVQGSGCFGRKMDRISSSSGLGCKVLRRH | 18.04 (4.68) | 2.14 (7.06) |
| 82) C18-KKGGG-BNP | $CH_3(CH_2)_{16}$COKKGGGSPKMVQGSGCFGRKMDRISSS SGLGCKVLRRH | 282.58 (34.04) | 343.62 (55.24) |
| 52) C18-KKKGGG-BNP | $CH_3(CH_2)_{16}$COKKKGGGSPKMVQGSGCFGRKMDRIS SSSGLGCKVLRRH | 801.3 (93.1) | 653.17 (67.48) |
| 113) C24-KKKKGG G-BNP | $CH_3(CH_2)_{22}$COKKKKGGGSPKMVQGSGCFGRKMDRI SSSSGLGCKVLRRH | 119.14 (36.08) | 108.33 (34.96) |
| 57) CNP | GLSKGCFGLKLDRIGSMSGLGC | 93.75 (9.85) | 24.55 (5.39) |
| 72) C18KKKK GGG-CNP | $CH_3(CH_2)_{16}$COKKKKGGGGLSKGCFGLKLDRIGSMSG LGC | 544.99 (119.32) | 368.29 (47.63) |
| 60) GGG-CNP | GGGGLSKGCFGLKLDRIGSMSGLGC | 49.98 (24.34) | 16.85 (11.74) |
| 58) G-CNP | GGLSKGCFGLKLDRIGSMSGLGC | 27.09 (15.60) | 5.10 (6.27) |
| 86) C18-KKGGG-CNP | $CH_3(CH_2)_{16}$COKKGGGGLSKGCFGLKLDRIGSMSGLG C | 80.2 (15.69) | 42.37 (1.49) |
| 68) C18-KKKGGG-CNP | $CH_3(CH_2)_{16}$COKKKGGGGLSKGCFGLKLDRIGSMSGL GC | 330.29 (35.56) | 250.33 (16.29) |
| 122) C24-KKKKGG G-CNP | $CH_3(CH_2)_{22}$COKKKKGGGGLSKGCFGLKLDRIGSMSG LGC | 251.92 (85.08) | 209.24 (47.4) |

As used herein, the 1.5 mg/kg dose for humans should also be equivalent to the 15 mg/Kg in mice as presented in the relevant data examples, which is equivalent to about 7.5 mg/Kg rat dose, which is equivalent to about 2.5 mg/Kg dog dose, which is equivalent to about 1.5 mg/Kg human dose. Because the mice response to 15 mg/Kg was quite high for the newly discovered derivatives (see Table 2) it will be prudent to use doses that are lower than 15 mg/Kg for mice, 7.5 mg/Kg for rat, 2.5 mg/Kg for dog, and 1.5 mg/Kg for human since any higher dose may result in too much increase in cGMIP that can result in too much or even dangerous drop in blood pressure unless formulated in a very slow release delivery system. In fact because the level of cGMIP at 2 hours is about five times prior to background subtraction it is even more prudent for the purpose of safety to use less than 3 mg/Kg for mice, 1.5 mg/Kg for rat, 0.5 mg/Kg for dog, and 0.3 mg/Kg for human. These doses are conservative guidelines in terms of not to exceed and are presented here with certainty. These newly disclosed compositions should be used at doses that are lower than native natriuretic peptide doses under a similar treatment condition because of higher potency. This higher potency translate to advantages in terms of requiring less material or lower cost, and smaller volume of drug administered or less pain for the patients. However, the exact human therapeutic dose of how much below the weight equivalent parent natriuretic dose cannot be predicted and is not obvious until human clinical safety trial data is available. Although the process of allometric scaling is predictive in general in adjusting dose from animals to human, the fine tuning of the dose for the purpose of safety in human cannot be done using allometric scaling alone. Nevertheless, allometric scaling is sufficient to estimate the highest possible safe starting dose to obtain therapeutic effect.

While the preferred embodiment of the disclosure has been illustrated and described, it will be appreciated that various changes can be made therein without departing from the spirit and scope of the disclosure.

---

The embodiments of the disclosure in which an exclusive property or privilege is claimed are defined as follows:

1. A composition comprising a natriuretic peptide derivative, wherein the natriuretic peptide derivative comprises SEQ ID NO: 9, SEQ ID NO: 10, SEQ ID NO: 11, SEQ ID NO: 14, SEQ ID NO: 18, SEQ ID NO: 52, SEQ ID NO: 56, SEQ ID NO: 68, SEQ ID NO: 72, SEQ ID NO: 86, SEQ ID NO: 94, SEQ ID NO: 95, SEQ ID NO: 113, or SEQ ID NO: 122.

2. The composition according to claim 1, wherein the natriuretic peptide derivative is selected from the group consisting of SEQ ID NO: 9, SEQ ID NO: 10, SEQ ID NO: 11, SEQ ID NO: 14, SEQ ID NO: 18, SEQ ID NO: 56, SEQ ID NO: 52, SEQ ID NO: 113, SEQ ID NO: 68, SEQ ID NO: 122, and SEQ ID NO: 72.

3. The composition according to claim 1, wherein the natriuretic peptide derivative is selected from the group consisting of SEQ ID NO: 9, SEQ ID NO: 10, SEQ ID NO: 11, SEQ ID NO: 14, SEQ ID NO: 18, SEQ ID NO: 56, and SEQ ID NO: 72.

4. The composition according to claim 1, wherein the natriuretic peptide derivative is selected from the group consisting of SEQ ID NO: 14, SEQ ID NO: 18, SEQ ID NO: 56, SEQ ID NO: 52, SEQ ID NO: 68, SEQ ID NO: 122, and SEQ ID NO: 72.

5. The composition according to claim 1, further comprising an excipient.

6. The composition of claim 1, wherein the natriuretic peptide derivative is, SEQ ID NO: 9, SEQ ID NO: 10, SEQ ID NO: 11, SEQ ID NO: 14, SEQ ID NO: 18, SEQ ID NO: 52, SEQ ID NO: 56, SEQ ID NO: 68, SEQ ID NO: 72, SEQ ID NO: 94, SEQ ID NO: 95, SEQ ID NO: 113, or SEQ ID NO: 122.

7. A method of increasing blood cGMP in a patient, the method comprising parenterally administering to the patient a composition according to claim 1.

* * * * *